(12) United States Patent
Sekowski

(10) Patent No.: US 10,835,360 B2
(45) Date of Patent: Nov. 17, 2020

(54) ADVANCED PERIODONTAL ENDOSCOPE AND METHODS

(71) Applicant: Research and Development International Corporation, Pasadena, CA (US)

(72) Inventor: Marek Sekowski, Pacific Palisades, CA (US)

(73) Assignee: Research and Development International Corporation, Pasadena, CA (US)

( * ) Notice: Subject to any disclaimer, the term of this patent is extended or adjusted under 35 U.S.C. 154(b) by 371 days.

(21) Appl. No.: 15/470,871

(22) Filed: Mar. 27, 2017

(65) Prior Publication Data

US 2017/0280986 A1 Oct. 5, 2017

Related U.S. Application Data

(60) Provisional application No. 62/316,660, filed on Apr. 1, 2016.

(51) Int. Cl.
*A61B 1/24* (2006.01)
*H04N 5/225* (2006.01)
(Continued)

(52) U.S. Cl.
CPC ........ *A61C 19/043* (2013.01); *A61B 1/00009* (2013.01); *A61B 1/00124* (2013.01);
(Continued)

(58) Field of Classification Search
CPC combination set(s) only.
See application file for complete search history.

(56) References Cited

U.S. PATENT DOCUMENTS 8,947,514 B2 2/2015 Shibasaki
2004/0092792 A1 5/2004 Kobayashi
(Continued)

FOREIGN PATENT DOCUMENTS

WO 2012003430 A2 1/2012

OTHER PUBLICATIONS

The International Search Report and The Written Opinion of the International Searching Authority for International Application No. PCT/US2017/025198 which is associated with U.S. Appl. No. 15/470,871, dated Jul. 31, 2017, Daejeon, Republic of Korea.

*Primary Examiner* — Mulugeta Mengesha
*Assistant Examiner* — Alazar Tilahun
(74) *Attorney, Agent, or Firm* — Pritzkau Patent Group LLC

(57) ABSTRACT

A periodontal endoscope includes an imaging handle having an imaging end that supports a camera sensor and an introducer including an introducer blade such that the introducer blade is selectively rotatable about the camera sensor for engaging gingival tissue in the field of view for any rotational orientation of the introducer blade relative to the camera while illuminated by an optical fiber bundle. An automatic illuminance controller controls an illumination light source at least within each frame as the frame is scanned based on dynamic range of the camera sensor such that high intensity areas of the frame receive a reduced amount of illumination light by reducing the illumination drive signal as compared to low intensity areas of the frame which receive an increased amount of illumination light by increasing the illumination drive signal relative to the high intensity areas.

19 Claims, 20 Drawing Sheets

(51) Int. Cl.
   *A61B 1/00* (2006.01)
   *A61C 19/04* (2006.01)
   *A61B 1/04* (2006.01)
   *A61B 1/06* (2006.01)
   *A61B 1/07* (2006.01)
   *G02B 23/24* (2006.01)
   *A61B 1/015* (2006.01)
   *A61B 1/247* (2006.01)
   *A61B 1/05* (2006.01)
   *B23K 26/00* (2014.01)

(52) U.S. Cl.
   CPC ...... *A61B 1/00128* (2013.01); *A61B 1/00135* (2013.01); *A61B 1/015* (2013.01); *A61B 1/05* (2013.01); *A61B 1/0607* (2013.01); *A61B 1/07* (2013.01); *A61B 1/247* (2013.01); *H04N 5/2252* (2013.01); *H04N 5/2256* (2013.01); *B06B 2201/76* (2013.01); *B23K 26/0096* (2013.01); *G02B 23/2469* (2013.01); *G02B 23/2484* (2013.01); *H04N 2005/2255* (2013.01)

(56) References Cited

U.S. PATENT DOCUMENTS

| | | | |
|---|---|---|---|
| 2008/0070189 A1* | 3/2008 | Turner | A61C 1/05 433/132 |
| 2012/0040305 A1* | 2/2012 | Karazivan | A61B 1/00087 433/29 |
| 2012/0123213 A1 | 5/2012 | Seto | |
| 2014/0099597 A1* | 4/2014 | Bergheim | A61C 17/02 433/80 |
| 2015/0348320 A1* | 12/2015 | Pesach | A61C 9/0033 382/128 |
| 2015/0359581 A1 | 12/2015 | Albertal | |
| 2016/0338803 A1* | 11/2016 | Pesach | G06T 1/0007 |
| 2017/0122525 A1* | 5/2017 | Root | G02B 6/4269 |

* cited by examiner

HIGH SPEED AUTOMATIC LUMINANCE CONTROL SYSTEM

ADVANCED PERIODONTAL ENDOSCOPE AND METHODS

RELATED APPLICATION

The present application claims priority from U.S. Provisional Patent Application Ser. No. 62/316,660 filed on Apr. 1, 2016, the disclosure and figures of which are hereby incorporated by reference in their entirety.

BACKGROUND

The present application is at least generally related to the field of dental devices and, more particularly, to an advanced periodontal endoscope and associated methods.

Untreated gingivitis can advance to periodontal disease which is characterized by inflammation and bleeding in the gums around the teeth. As the disease progresses, the gums pull away from the teeth and form pockets that become infected. With further progression, toxins are produced as plaque spreads and grows below the gum line. These bacterial toxins and the natural response of the body can cause loss of connective tissue that hold the teeth in place as well as loss of surrounding bone. The teeth may ultimately become loose and, without treatment, be lost.

A periodontal endoscope is a device that allows a dentist or hygienist to image the area under the gum deep around the root of the tooth for purposes of assessment and the application of therapy, for example, relating to periodontal disease. A perioscope generally includes an introducer blade that is used at least to move the marginal gingival tissue away from the tooth to provide for viewing therebelow, for example, of the attached gingival region in order to assess the condition of the tissue. Some periodontal endoscopes provide for irrigation, for example, to remove treatment debris and blood from the field of view.

Applicants recognize that prior art periodontal endoscopes exhibit limitations that, until now, have remained unresolved. The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In general, a periodontal endoscope and associated methods are described. In one aspect of the disclosure, the periodontal endoscope includes an imaging handle having a grip portion intermediate between a connection end and an imaging end, the imaging end including a tubular housing that supports a camera sensor therein for imaging a field of view. The connection end at least configured for external electrical connection for providing external electrical power to the camera sensor and for transferring electrical signals including electrical image signals based on imaging of the field of view by the camera sensor to the connection end for external transfer. An introducer includes an introducer blade and defines a camera channel that receives the camera sensor such that the introducer blade is selectively rotatable about the camera for engaging gingival tissue in the field of view for any rotational orientation of the introducer blade relative to the camera. An illumination arrangement includes an optical fiber bundle that extends from the connection end to the imaging end for carrying illumination light that is introduced into the optical fiber bundle at the connection end and emitted from the optical fiber bundle at the imaging end to illuminate the field of view.

In another aspect of the disclosure, the periodontal endoscope forms a periodontal endoscopic imaging system along with a console. The console includes a display for displaying the field of view.

based on the electrical image signals. An illumination light source produces illumination light that is coupled to an umbilical to carry the illumination light to an umbilical connector that is complementary to the connection end of the imaging handle to couple the illumination light into the optical fiber bundle when the umbilical connector is removably attached to the connection end.

In still another aspect of the present disclosure, an endoscope includes an imaging arrangement for imaging an image area proximate to a distal end of the endoscope to produce a video image stream having a series of frames that is transferred to a proximal end of the endoscope for viewing by an operator, the imaging arrangement configured to produce the video image stream based on a limited dynamic range. An illumination arrangement includes an illumination light source to produce an illumination light that illuminates the image area at an illumination level that is controllable responsive to an illumination drive signal. An automatic luminance controller generates the illumination drive signal to modulate the illumination light source at least within each frame as the frame is scanned based on the dynamic range such that high intensity areas of the frame receive a reduced amount of illumination light by reducing the illumination drive signal as compared to low intensity areas of the frame which receive an increased amount of illumination light by increasing the illumination drive signal relative to the high intensity areas.

In yet another aspect of the present disclosure, an endoscope includes an imaging arrangement for scanning an image area proximate to a distal end of the endoscope to produce a video image stream having a series of frames that is transferred to a proximal end of the endoscope for viewing by an operator, the imaging arrangement is configured to produce the video image stream based on a limited dynamic range. An illumination arrangement includes an illumination light source to produce an illumination light that illuminates the image area at an illumination level that is controllable responsive to an illumination drive signal. An automatic luminance controller is configured to generate the illumination drive signal responsive to scanning of the image area by selectively illuminating the image area such that each unit of a plurality of units that make up each frame receives a selected illumination value based on adjusting the illumination drive signal on a unit-by-unit basis during each scan.

In a continuing aspect of the present disclosure, an endoscope includes an imaging arrangement for scanning an image area proximate to a distal end of the endoscope to produce a video image stream having a series of frames that is transferred to a proximal end of the endoscope for viewing by an operator, the imaging arrangement is configured to produce the video image stream based on a limited dynamic range. An illumination arrangement includes an illumination light source to produce an illumination light that illuminates the image area at an illumination level that is controllable responsive to an illumination drive signal. An automatic luminance controller generates the illumination drive signal based on an illumination compensation template that specifies an illumination value for each one of a plurality of units of each frame such that the image area is illuminated for each unit, responsive to the illumination drive signal, at a corresponding illumination value that is taken from the illumination compensation template, as each unit of each frame is scanned by the imaging arrangement.

In a further aspect of the present disclosure, a method for operating an endoscope is described including scanning an image area proximate to a distal end of the endoscope to produce a video image stream having a series of frames that is transferred to a proximal end of the endoscope for viewing by an operator, the imaging arrangement configured to produce the video image stream based on a limited dynamic range. The image area is illuminated at an illumination level that is controllable responsive to an illumination drive signal. The illumination level is modulated at least within each frame as the frame is scanned based on the dynamic range such that high intensity areas of the frame receive a reduced amount of illumination light by reducing the illumination drive signal as compared to low intensity areas of the frame which receive an increased amount of illumination light by increasing the illuminating drive signal relative to the high intensity areas.

BRIEF DESCRIPTIONS OF THE DRAWINGS

Example embodiments are illustrated in referenced figures of the drawings. It is intended that the embodiments and figures disclosed herein are illustrative rather than limiting.

DETAILED DESCRIPTION

Figure 1:
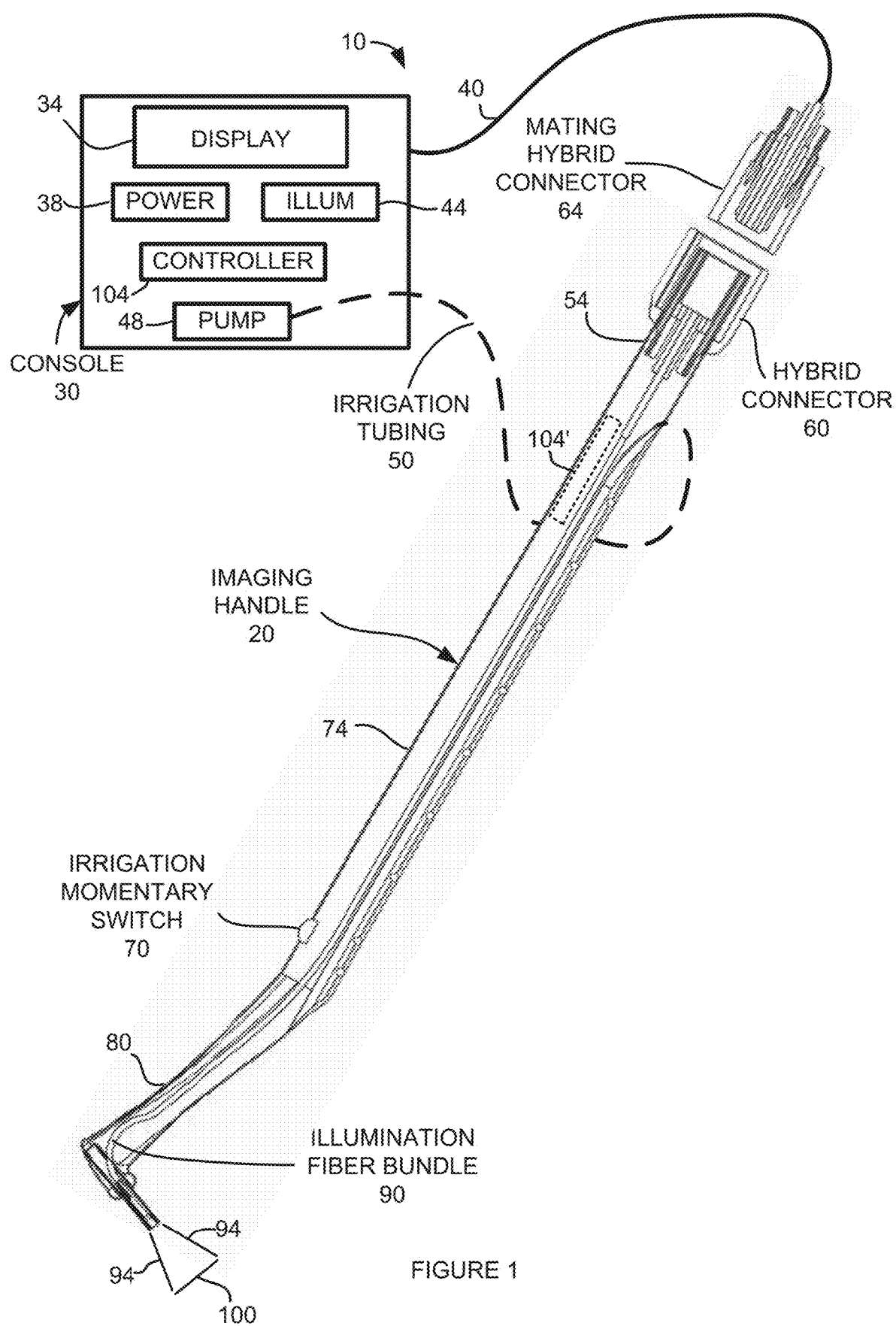
FIG. 1 is a diagrammatic view, in elevation, of a periodontal endoscope system in accordance with an embodiment of the present disclosure.

The following description is presented to enable one of ordinary skill in the art to make and use the invention and is provided in the context of a patent application and its requirements. Various modifications to the described embodiments will be readily apparent to those skilled in the art and the generic principles taught herein may be applied to other embodiments. Thus, the present invention is not intended to be limited to the embodiment shown, but is to be accorded the widest scope consistent with the principles and features described herein including modifications and equivalents. It is noted that the drawings are not to scale and are diagrammatic in nature in a way that is thought to best illustrate features of interest. Descriptive terminology may be adopted for purposes of enhancing the reader's understanding, with respect to the various views provided in the figures, and is in no way intended as being limiting.

Embodiments of a periodontal endoscope, in accordance with the present disclosure, streamline functionality of the device by separating an imaging and illumination assembly from a disposable introducer and irrigator. In one feature, an introducer and irrigator are integrated into a very small plastic component that can be fabricated as a disposable element. An imaging handle is separately formed and includes a camera assembly with a camera housing and associated optics extending from a distal end of the imaging handle. The new introducer/irrigator (which may be referred to hereinafter as an introducer) can be attached to the imaging handle assembly, for example, in a snap-on fashion by receiving the camera assembly into a channel that is defined by the introducer such that the camera images the tip of the introducer. After the introducer is secured on the imaging handle, the introducer can be rotated relative to the camera assembly so the orientation of a blade can be adjusted to correspond to the direction of the gum line. As compared to prior art periodontal endoscopes, this adjustment feature eliminates the need for switching between four introducers each of which presents the blade in a different orientation for differing sections of the patient's mouth. Subsequent to the procedure, the imaging handle can be separated from the introducer/irrigator while the imaging handle can be separated from a cable that connects the imaging handle to a console. The introducer/irrigator can be produced at low cost to facilitate disposability while the sealed imaging handle can be autoclaved for reuse.

In embodiments according to the present disclosure, an imaged area can be enlarged up to 50 times so the dentist or hygienist has no need for a prior art optical loop or magnifying googles that typically restrict the motion of the head and can cause pain and prolonged problems in the neck. Among other benefits, a user of the periodontal endoscope brought to light herein is free to change the position/orientation of the head of the periodontal endoscope, thereby avoiding physical stress to the operator. The periodontal endoscope disclosed herein can be used, for example, in conjunction with another device such as an ultrasonic cleaner to assure that a cleaning procedure was complete and thorough.

The reader's attention is now directed to FIG. 1 which is a diagrammatic, partially cutaway view, in elevation, of an embodiment of a periodontal endoscope system, generally indicated by the reference number 10, which includes a periodontal endoscope imaging handle 20 and a console 30. The latter includes a display 34 at least for displaying video, a power supply 38 for providing electrical power to imaging handle 20 through an umbilical 40, an illumination source 44 such as, for example, an LED illumination source that can be modulated so as to control its output intensity and an irrigation pump 48 that can provide a flow of irrigation fluid to the imaging handle through an irrigation tube 50. It is noted that the irrigation tube is shown in phantom using dashed lines since the irrigation tubing forms part of a rotatable snap-on introducer, yet to be described. Imaging handle 20 includes a proximal end 54 supporting a hybrid connector 60 that is complementary to a mating hybrid connector 64. The hybrid connector arrangement will be described in detail below. For the moment, it is sufficient to note that connectors 60 and 64 facilitate the transfer of illumination light, imaging data and any other electrical signals that are needed. As an example of the latter, an irrigation switch 70 can couple through a set of electrical contacts in connectors 60 and 64 such that switch actuation causes irrigation pump 48 to run. This switch generally is a momentary contact switch such that the irrigation pump is on only during active operator engagement of switch 70. The irrigation switch can be provided on an intermediate portion 74 of the imaging handle between proximal end 54 and a distal end 80. An illumination optical fiber bundle carries illumination light that is generated by illumination source 44, carried through umbilical 40, for example, by a segment of optical fiber bundle and coupled to an illumination fiber bundle 90 such that illumination light 94 is emitted onto a viewing area 100. A controller 104 can be supported at any suitable location such as, for example, in console 30 and interfaced to a camera sensor, yet to be described, via umbilical 40 and imaging handle 20. In another embodiment, controller 104' (shown in phantom using dotted lines) can be located in imaging handle. In still another embodiment, the controller can be located in a camera housing or barrel, yet to be described, where the camera sensor is mounted.

Figure 2:
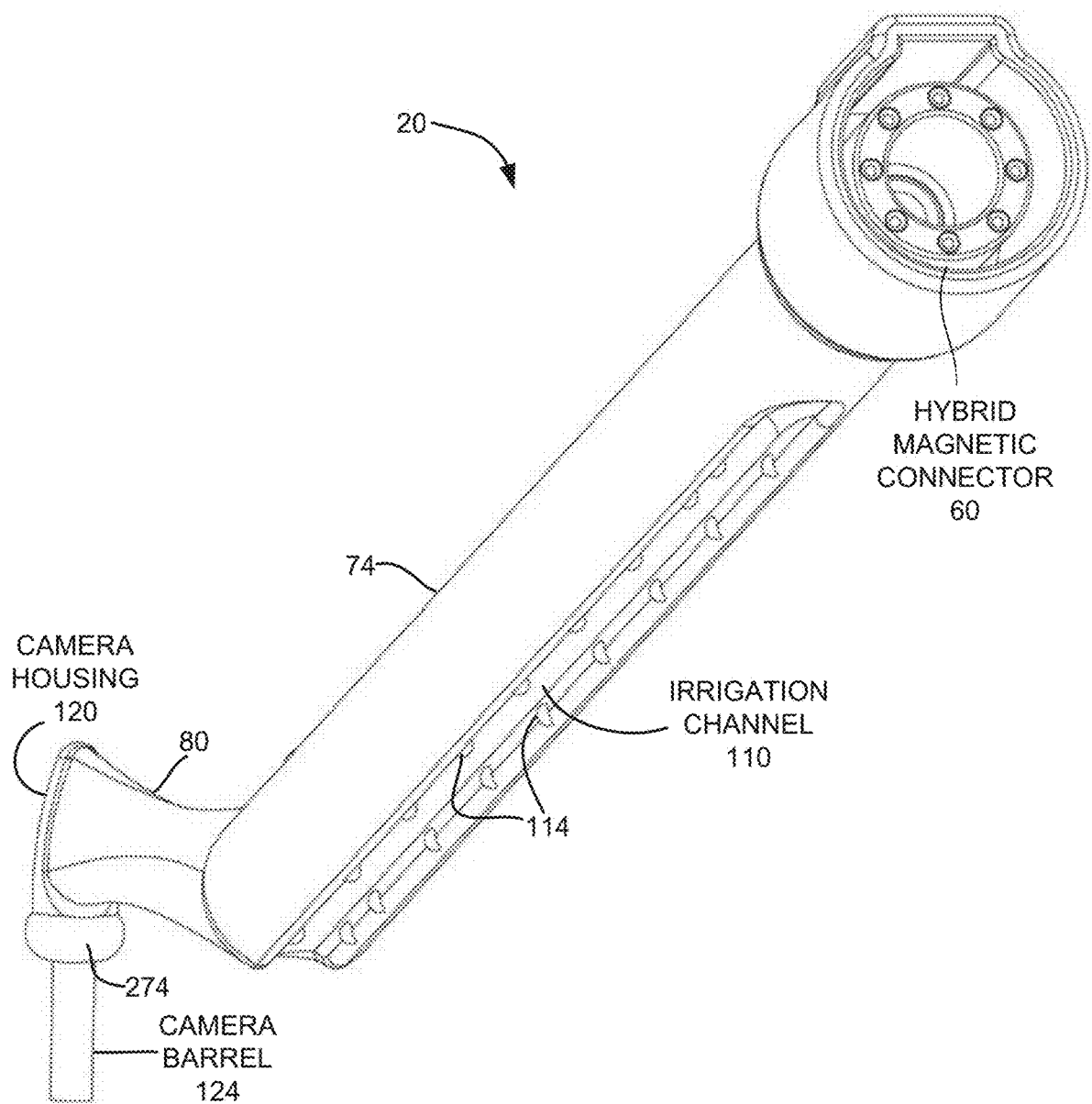
FIG. 2 is a diagrammatic partially cutaway view of an embodiment of an imaging handle of the periodontal endoscope system of FIG. 1, in perspective, showing additional details of its structure.

Referring to FIG. 2, in conjunction with FIG. 1, the former diagrammatically illustrates an embodiment of imaging handle 20 in a perspective view looking toward hybrid connector 60. The imaging handle can define an irrigation channel 110 that can receive irrigation tube 50 (FIG. 1), for example, using a snap-in configuration having a series of tabs 114 lining one or both sides of the channel to retain a portion of the length of the irrigation tube. Distal end 80 of the imaging handle fixedly supports a camera housing 120 from which a camera barrel 124 extends. The latter can be a hollow cylinder or tube or some other suitable shape. A camera sensor, for example, a CMOS camera or other suitable camera as well as other optics yet to be described can be received in the camera housing and barrel. It is noted that the main body of imaging handle 20 can be formed, for example, from materials that are suitable for autoclaving.

Figure 3:
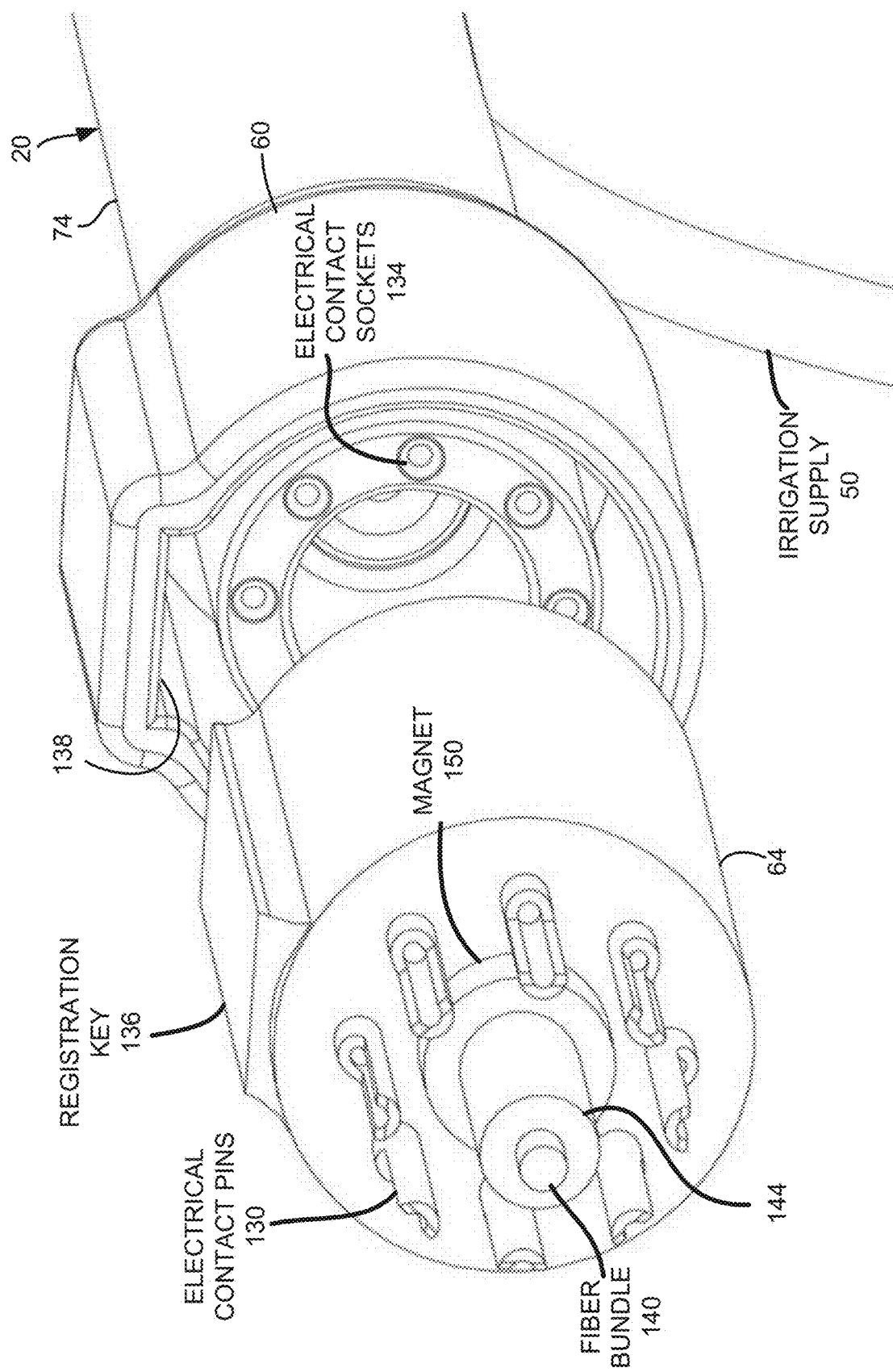
FIG. 3 is a diagrammatic view, in perspective, illustrating an embodiment of a hybrid connector arrangement with magnetic engagement and including a registration key and axial fiber lumen.

FIG. 3 is a diagrammatic fragmentary view, in perspective, illustrating an embodiment of a hybrid magnetic connector arrangement including hybrid connector 60 in a confronting relationship with mating hybrid connector 64. The view of this figure is taken from the rear of mating hybrid connector 62 and shows the connector arrangement in an unmated state. It is noted that the distal end of umbilical 40 (FIG. 1) has not been shown for purposes of illustrative clarity. Mating hybrid connector 64 includes a set of electrical contact pins 130 that can be arranged, for example, in a circular layout. A complementary layout of electrical contact sockets 134 can be seen supported in hybrid connector 60 for receiving pins 130. It should be appreciated that any suitable form of electrical contact can be utilized such as, for example, spring probe pins supported by mating hybrid connector 60 and contact pads supported by hybrid connector 64. A registration key 136 on the mating hybrid connector is receivable in a registration recess 138 that is defined by hybrid connector 60 for purposes of indexing pins 130 with sockets 134 during mating. An umbilical fiber bundle 140 (only partially shown) is supported in a fiber ferrule 144 for delivering illumination light from illumination source 44 to the hybrid connector arrangement. In the present embodiment, umbilical fiber bundle 140 and the layout of electrical contact pins are coaxial with a cylindrical body of mating hybrid connector 64. An umbilical magnet 150 is provided, for example, in the form of a ring for removable magnetic coupling of mating hybrid connector 64 to hybrid connector 60, as will be further described.

Figure 4:
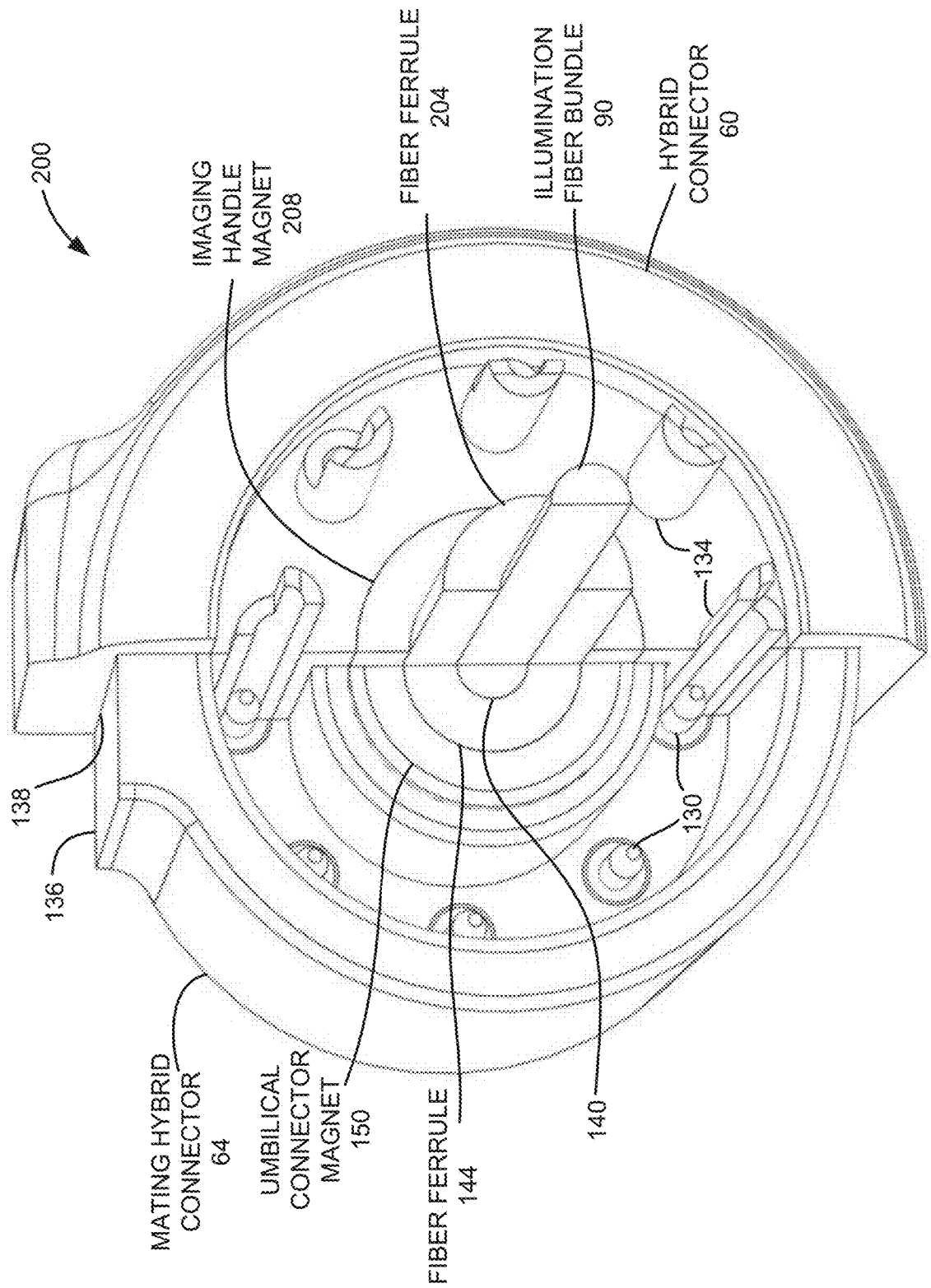
FIG. 4 is a diagrammatic partially cutaway view, in perspective, illustrating mating of the hybrid magnetic connector with a console side hybrid connector including what can be referred to as a magnetic ferrule or ring with a fiber bundle aligned axially therein.

FIG. 4 is a diagrammatic partially cutaway view, in perspective, illustrating an embodiment of the hybrid magnetic connector arrangement, generally indicated by the reference number 200. The view of FIG. 4 is taken from the rear of hybrid connector 60 and shows the connector arrangement in a mated state. This cutaway view shows one half of hybrid connector 60 including an end portion of illumination fiber bundle 90 and a ferrule 204 that supports the end of fiber bundle 90. An imaging handle magnet 208, in the form of a ring, is arranged for magnetic attraction to magnet 150 to magnetically removably attach the imaging handle to mating hybrid connector 64. In the mated state, an end face of umbilical fiber bundle 140 is optically butt coupled with an end face of illumination fiber bundle 90 such that illumination light is passed from the umbilical fiber to illumination fiber bundle 90. At the same time, electrical contact is made between pins 130 and sockets 134. It is noted that coupling between the umbilical hybrid connector and the imaging handle hybrid connector can be accomplished in any suitable manner including using other embodiments of magnetic coupling as well as through more conventional approaches such as, for example, using a locking ring that can carry a thread.

Figure 5:
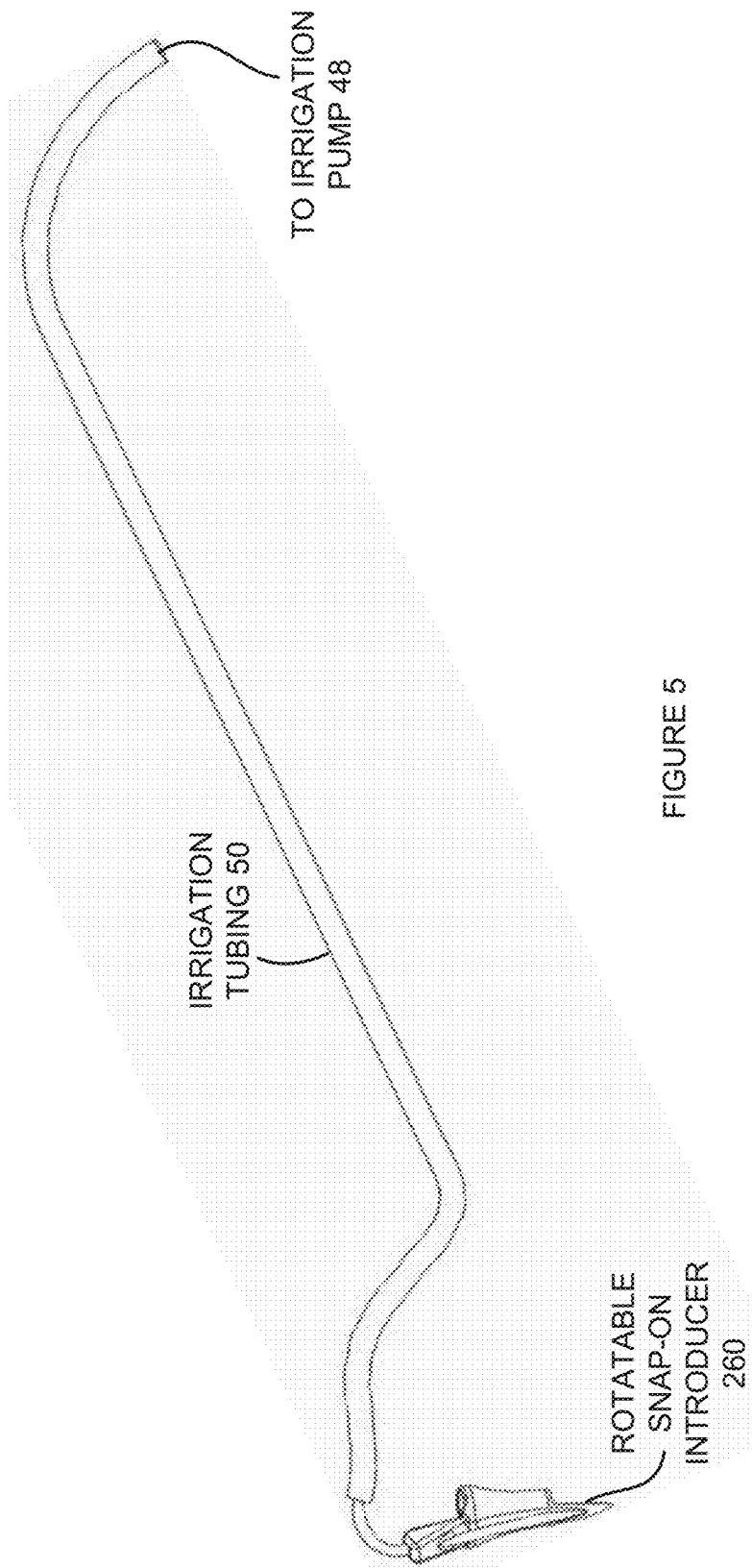
FIG. 5 is a diagrammatic view, in perspective, of an embodiment of a rotatable snap-on introducer according to the present disclosure with irrigation tubing.
Figure 6:
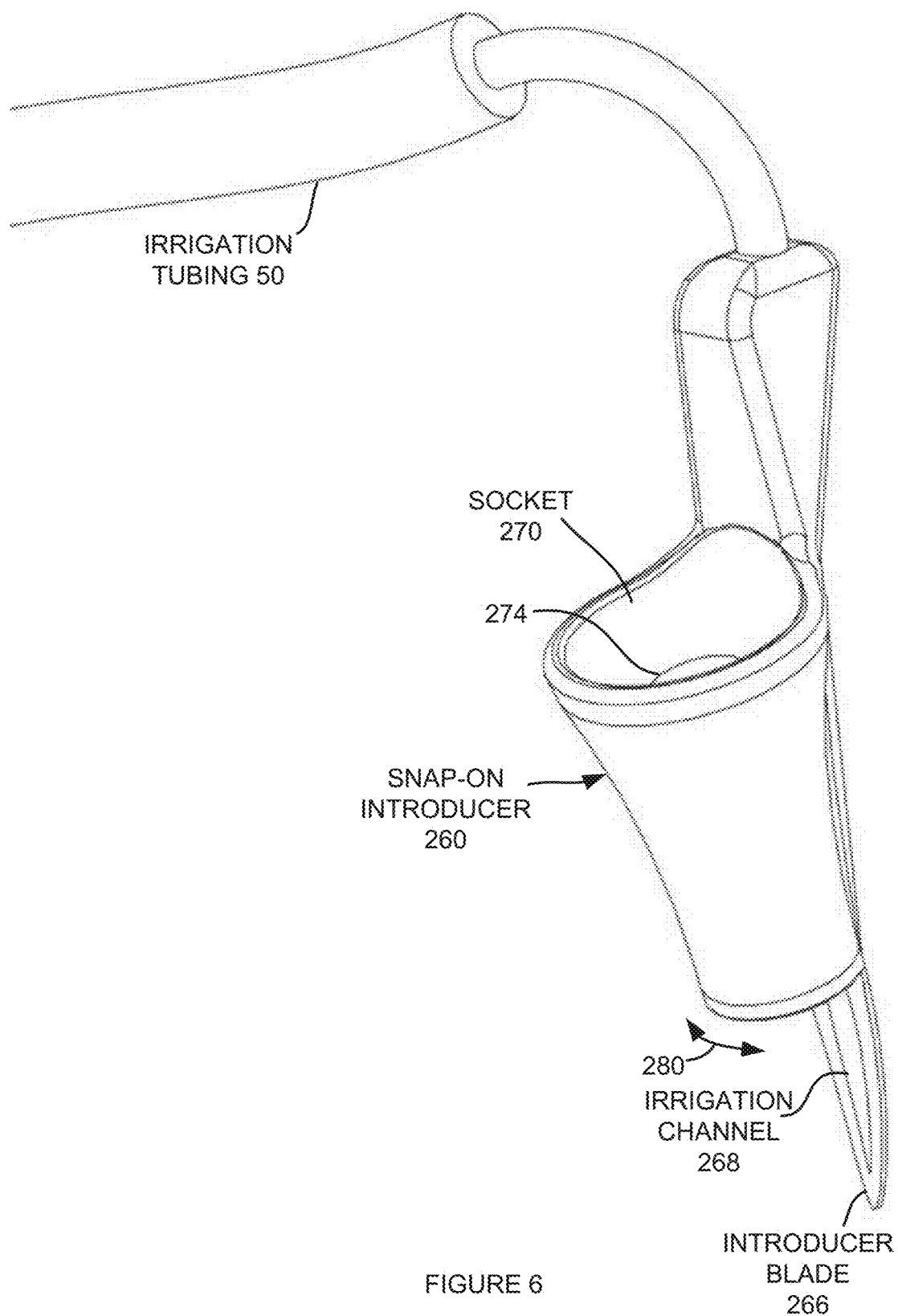
FIG. 6 is a further enlarged diagrammatic view, in perspective, of the embodiment of the introducer of FIG. 5 illustrating a snap-on rotatable socket or channel for receiving a camera assembly.
Figure 7:
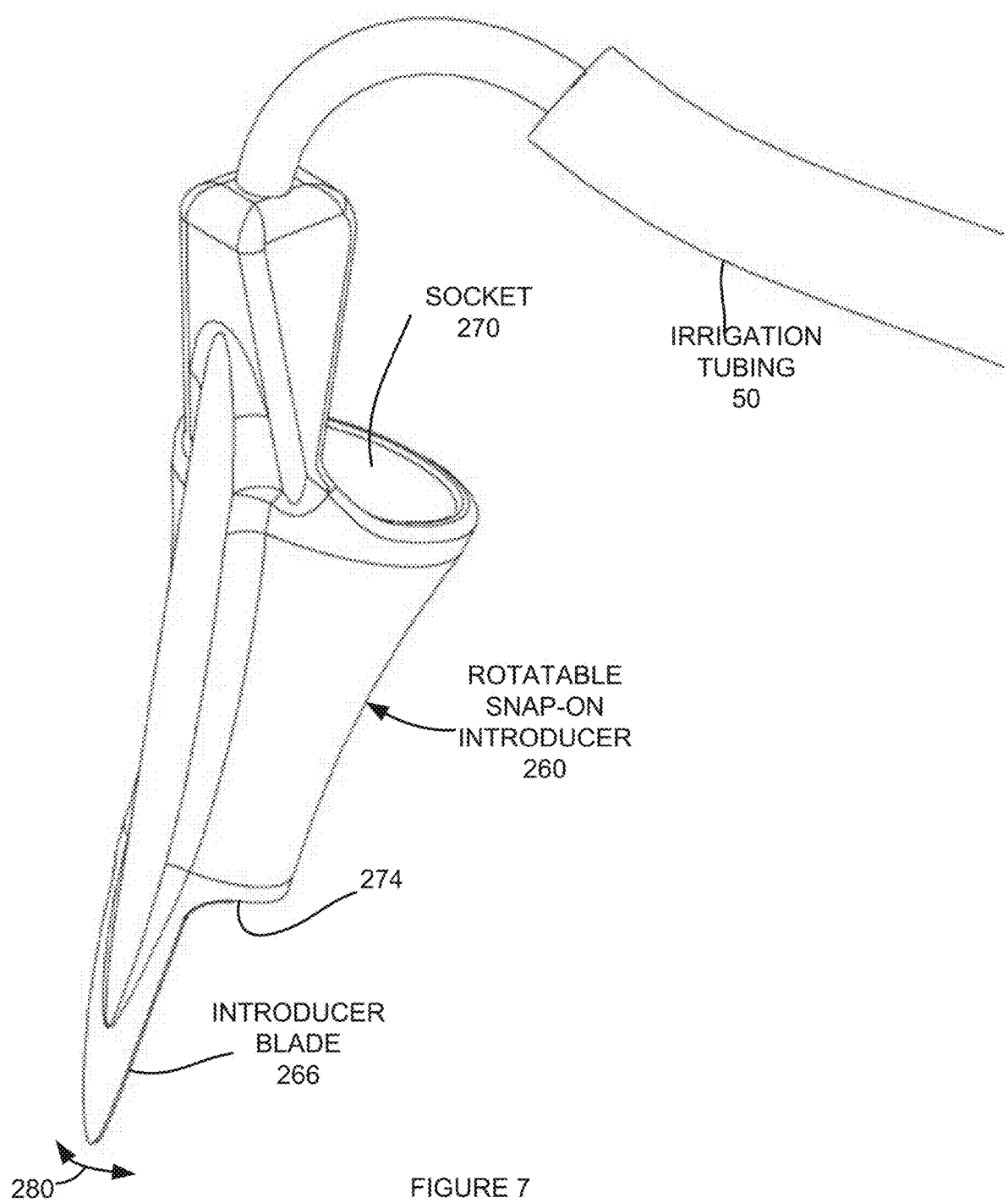
FIG. 7 is another further enlarged diagrammatic view of the embodiment of the introducer of FIG. 5, in another perspective, illustrating the snap-on rotating socket or channel for receiving the camera assembly.

FIG. 5 is a diagrammatic view, in perspective, illustrating an embodiment of a disposable rotatable snap-on introducer, indicated by the reference number 260 and produced in accordance with the present disclosure, from which irrigation tubing 50 extends to irrigation pump 48 in console 30. FIGS. 6 and 7 are further enlarged diagrammatic views, taken from differing perspectives, of the embodiment of introducer 260 shown in FIG. 5. The introducer includes an introducer blade 266 for engaging gingival tissue and an irrigation channel 268 (FIG. 6) that can be formed as a groove defined on an inner side of blade 266 for receiving the flow of irrigation fluid. Introducer 260 includes a socket 270 having a shape that is at least generally complementary to the shape of a bulb 274 (FIG. 2) to accomplish a snap fit therebetween. For instance, the sidewall of socket 270 can be curved slightly inward at its mouth. It is noted that many other cooperating complementary shapes can be developed with this overall disclosure in hand. Suitable shapes allow introducer 260 to rotate on the imaging handle without limitation. The engagement should be sufficient to allow an operator to set the introducer blade to a desired rotational orientation with relative ease and then use the imaging handle with the introducer in the desired rotational orientation such that engaging the introducer blade with the tissue of the patient does not produce undesired or unexpected rotation of the introducer on the imaging handle. In other words, the rotational orientation of the introducer is locked for purposes of performing a patient procedure and variable for purposes of operator adjustment, for example, to engage a different section of the patient's teeth. Below socket 270, the body of the introducer can define a cavity 274 (only partially visible in FIG. 6) that is complementary to the periphery of camera barrel 124 which can at least generally be cylindrical to provide for rotation of the introducer about the camera barrel, as indicated by a double headed arrow 280, as well as removable installation of the camera barrel into such a cavity. In this regard, suitable shapes for the camera barrel include, by way of non-limiting example, cylindrical and frustoconical. It is noted that the introducer blade and the snap-on introducer body can be formed from any suitable material such as, for example, a suitable plastic. One non-limiting example of a suitable plastic is PEEK.

Figure 8:
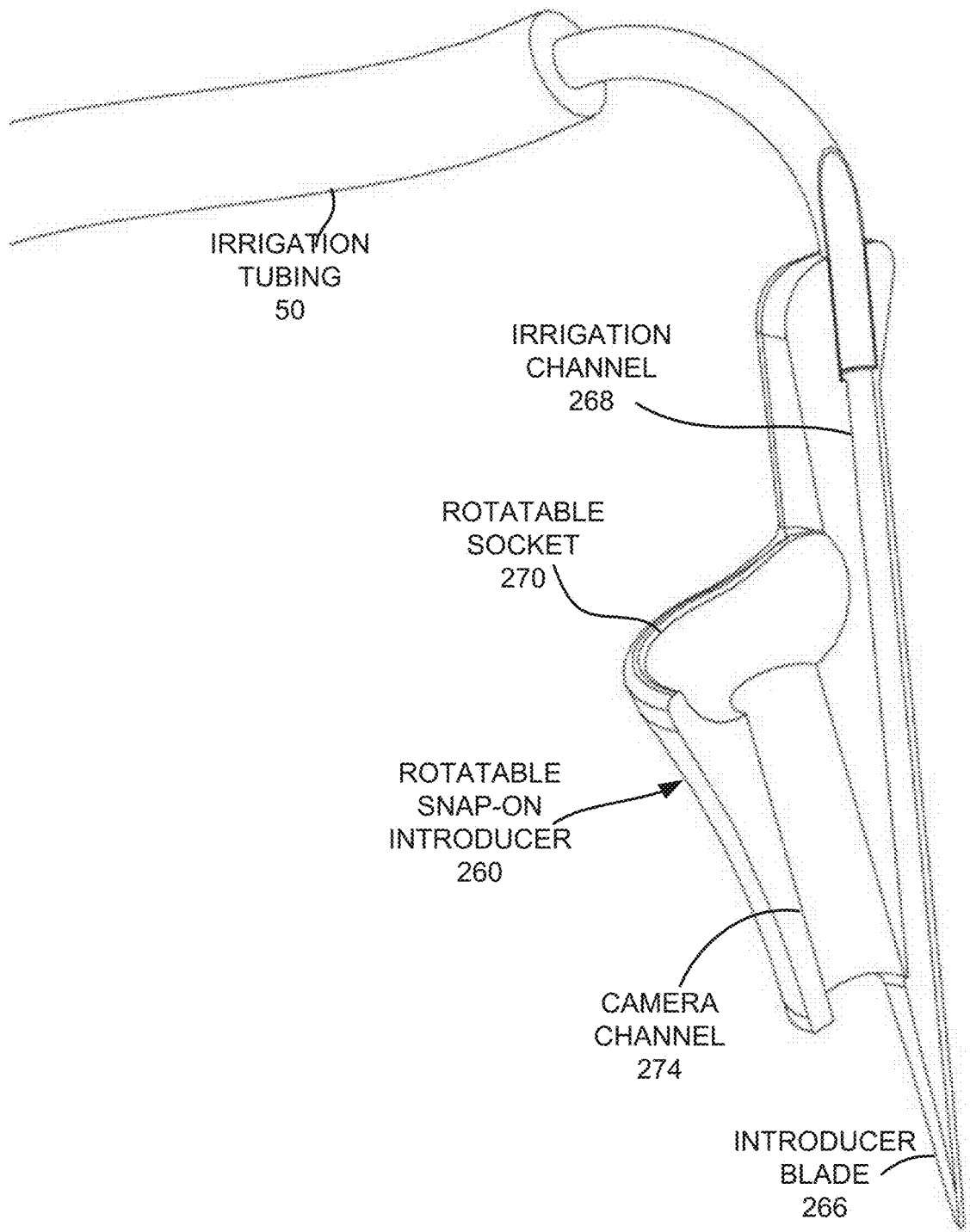
FIG. 8 is a diagrammatic cutaway view, in perspective, illustrating details of the embodiment of the introducer of FIGS. 5-7 showing a profile of a channel for receiving a camera assembly within a rotating socket and additionally illustrating an irrigation channel.

FIG. 8 is a further enlarged diagrammatic view, taken from essentially the same perspective as FIG. 6, of the embodiment of introducer 260 shown in FIG. 5, but with the introducer partially cutaway to illustrate additional details of its structure including irrigation channel 268 and a cylindrical embodiment of camera cavity 274. As will be seen in subsequent figures, camera cavity 274 can support additional optical components. As noted above, introducer 260 is disposable at least by virtue of the ability to produce it at low cost. In this regard, the introducer can be integrally molded from a suitable plastic, for example, as described above, with a suitable fitting for attachment of irrigation tubing 50.

Figure 9:
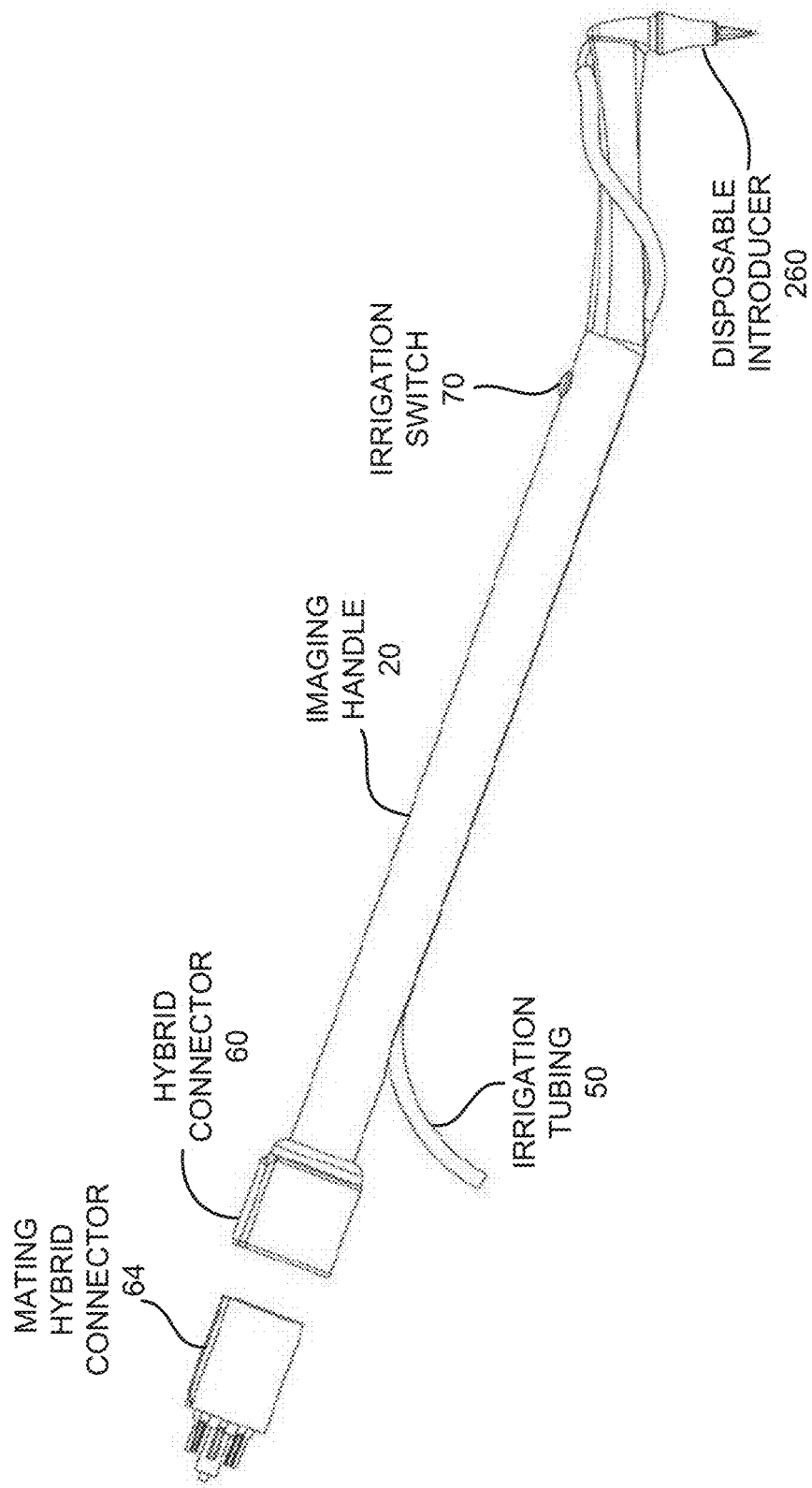
FIG. 9 is a diagrammatic view, in perspective, illustrating an embodiment of a periodontal endoscope assembly, imaging handle and disposable introducer in accordance with the present disclosure.
Figure 10:
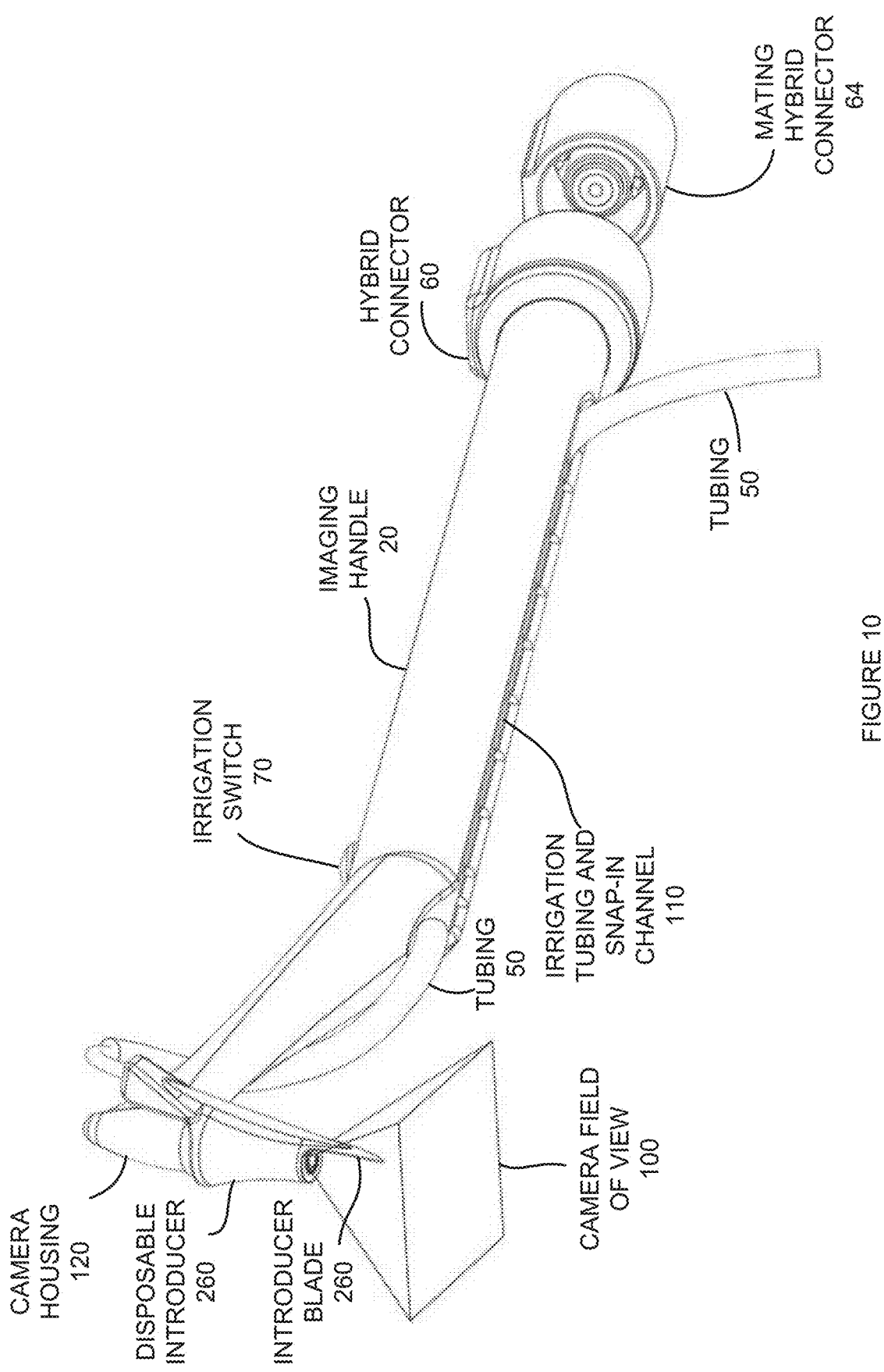
FIG. 10 is a diagrammatic view, in perspective, of the embodiment of the periodontal endoscope assembly of FIG. 9, taken from a different perspective to show additional details, for example, including a camera field of view.
Figure 11:
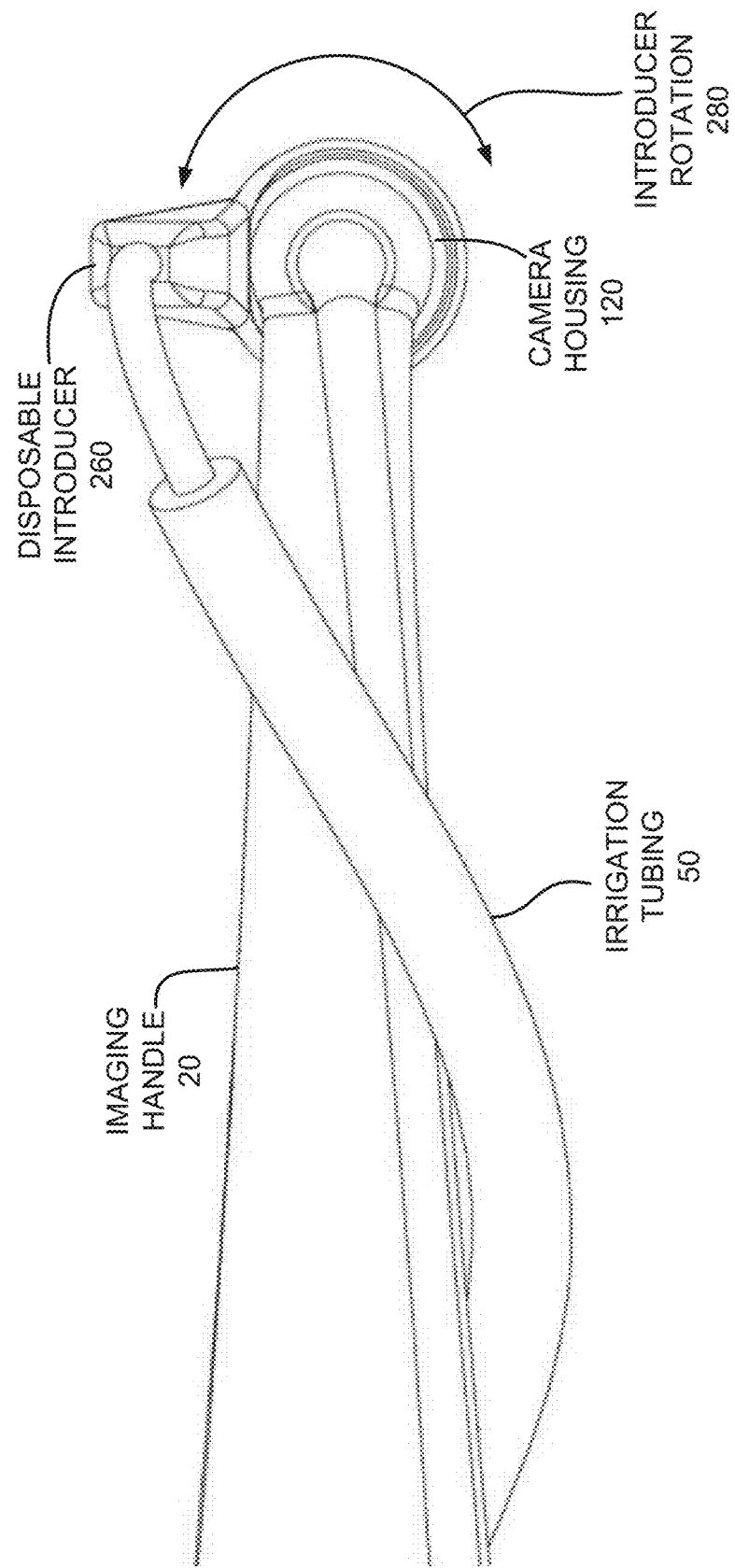
FIG. 11 is a further enlarged diagrammatic overhead view, in perspective, of the embodiment of the periodontal endoscope assembly of FIGS. 9 and 10 shown here at least to illustrate rotatability of the introducer relative to the camera assembly and imaging handle.

FIGS. 9 and 10 are diagrammatic views, taken from differing perspectives, of imaging handle 20 having disposable introducer 260 removably installed thereon in a manner that is consistent with the foregoing descriptions. FIG. 11 is a diagrammatic plan view of distal end 80 of imaging assembly 20 with introducer 260 removably installed to further illustrate introducer 280 rotation relative to camera housing 120. In this view, it should be clear that the introducer can be rotated by at least 320 degrees (+/−160 degrees). In some embodiments, a full range (360 degrees) can be provided, for example, by producing at least a portion of the introducer from a suitable flexible material and/or configuring the introducer to eliminate interference with the imaging handle responsive to rotation. With regard to rotation, Applicants are unaware of any prior art periodontal endoscope that provides for rotation by any amount, necessitating the use and manufacture of a set of different introducers each having a different blade orientation.

Figure 12:
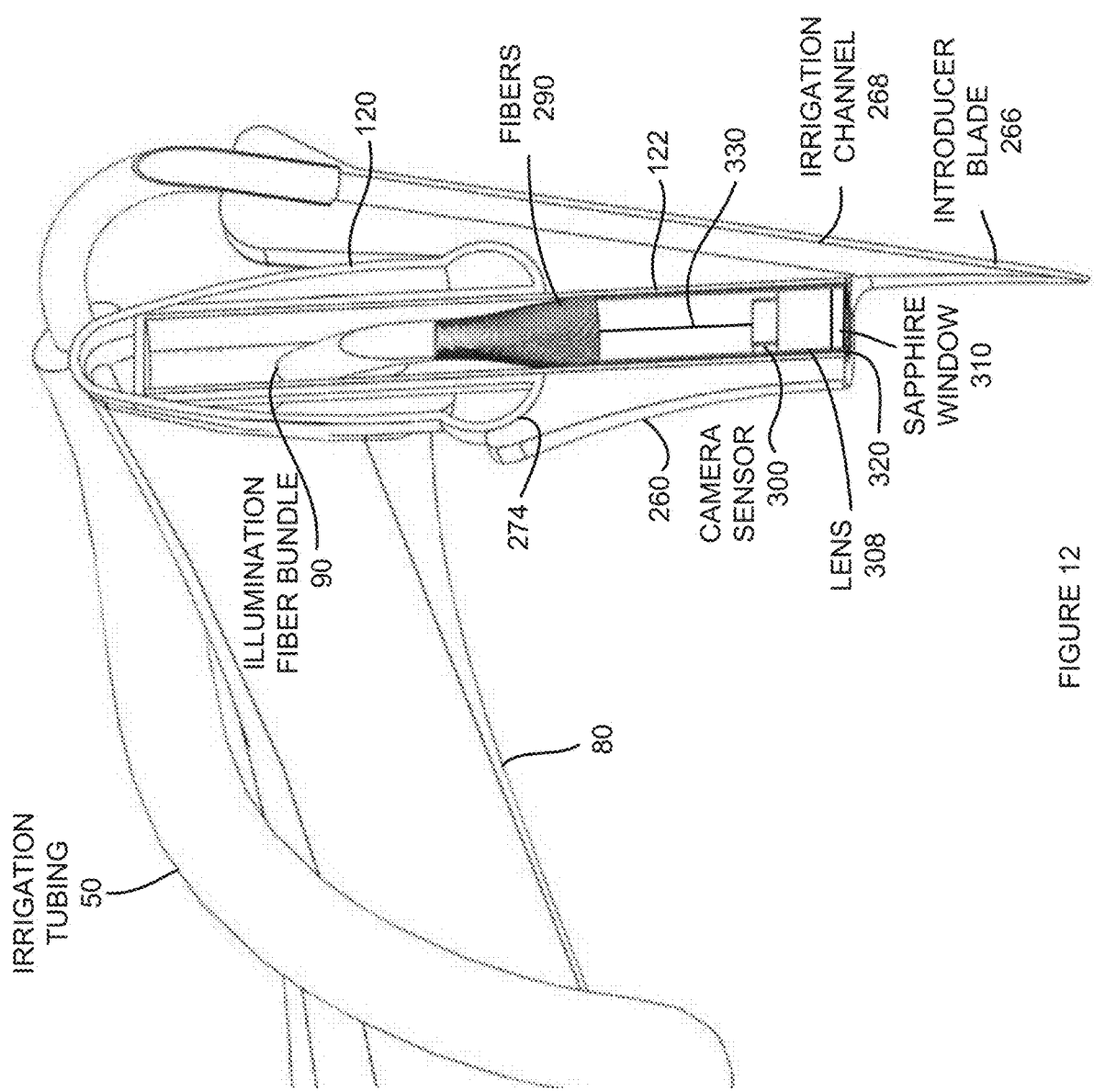
FIG. 12 is an enlarged diagrammatic cutaway view, in perspective, showing details of the distal end of the periodontal endoscope embodiment at least including a fiber illumination ring, a sapphire window, the profile of the blade, a lens objective, a camera sensor, an irrigation channel, an illumination fiber bundle, the snap-on rotating socket, and the camera head or assembly.

FIG. 12 is a diagrammatic fragmentary and partially cutaway view, in elevation, illustrating an embodiment of distal end 80 of imaging handle 20 with introducer 260 removably installed thereon, shown here to illustrate details with respect to camera housing 120 and components supported therein. In particular, illumination fiber bundle 90 enters camera housing 120 and extends downwardly in the view of the figure. Fibers 290 of the fiber bundle are separated and arranged around an outer periphery of a camera sensor 300, a lens 308 and a window 310 which can be formed, for example, from sapphire are supported by the cameral barrel with the ends of the fibers forming an annular fiber ring 320 proximate to a distal tip of cameral barrel 122, surrounding window 310, for illuminating the field of view. It is noted that camera barrel 122 is formed from a material that blocks the entry of stray light from potentially entering the camera sensor. The camera sensor can be of a suitable type either currently available or yet to be developed such as, for example, a CMOS sensor and can be interfaced with camera controller 104 (FIG. 1) that drives the sensor. In other embodiments, the annular ring of fibers can provide illumination through the same window that picks up the image light or a separate annular window can be provided. Electrical conductors 330, as needed, can provide electrical power to camera 320 and carry video imaging signals back to hybrid connector 60 for coupling to console 30. It should be appreciated that the image provided by the camera sensor can remain focused on the tip of blade 266 irrespective of the rotational position of the introducer relative to the camera barrel and the tip of the introducer blade can always remain at the center of the image, irrespective of rotational orientation, at least to a reasonable approximation.

Figure 13:
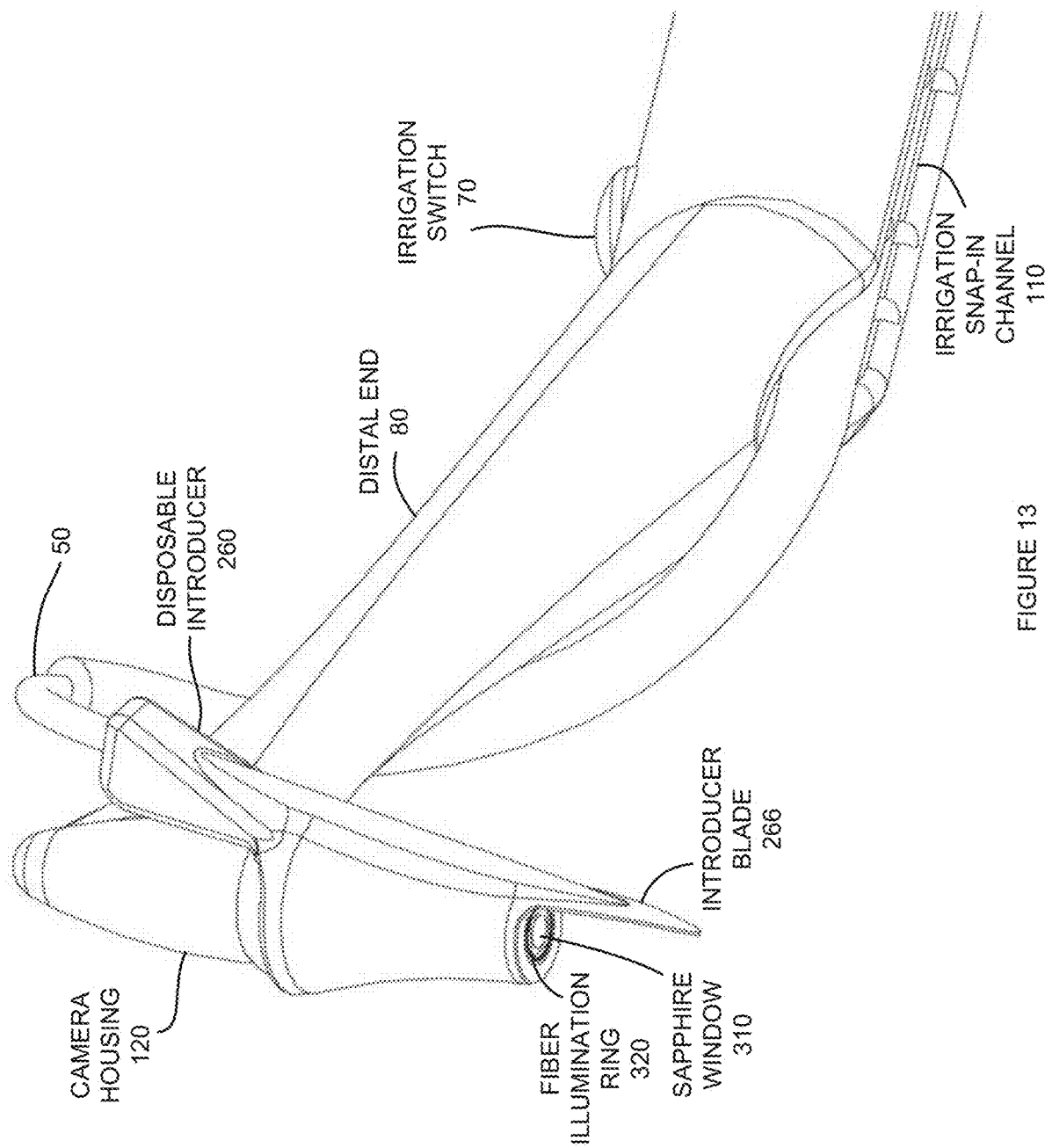
FIG. 13 is a diagrammatic view, in perspective, of the periodontal endoscope embodiment illustrating at least the installed irrigation tubing, the fiber illumination ring, the sapphire window and the camera housing installed in the introducer.

FIG. 13 is a diagrammatic fragmentary cutaway view, taken from a perspective looking at distal end 80 of the imaging handle, including camera window 310 of the embodiment of FIG. 12 with removable introducer 260 installed and with tubing 50.

Figure 14:
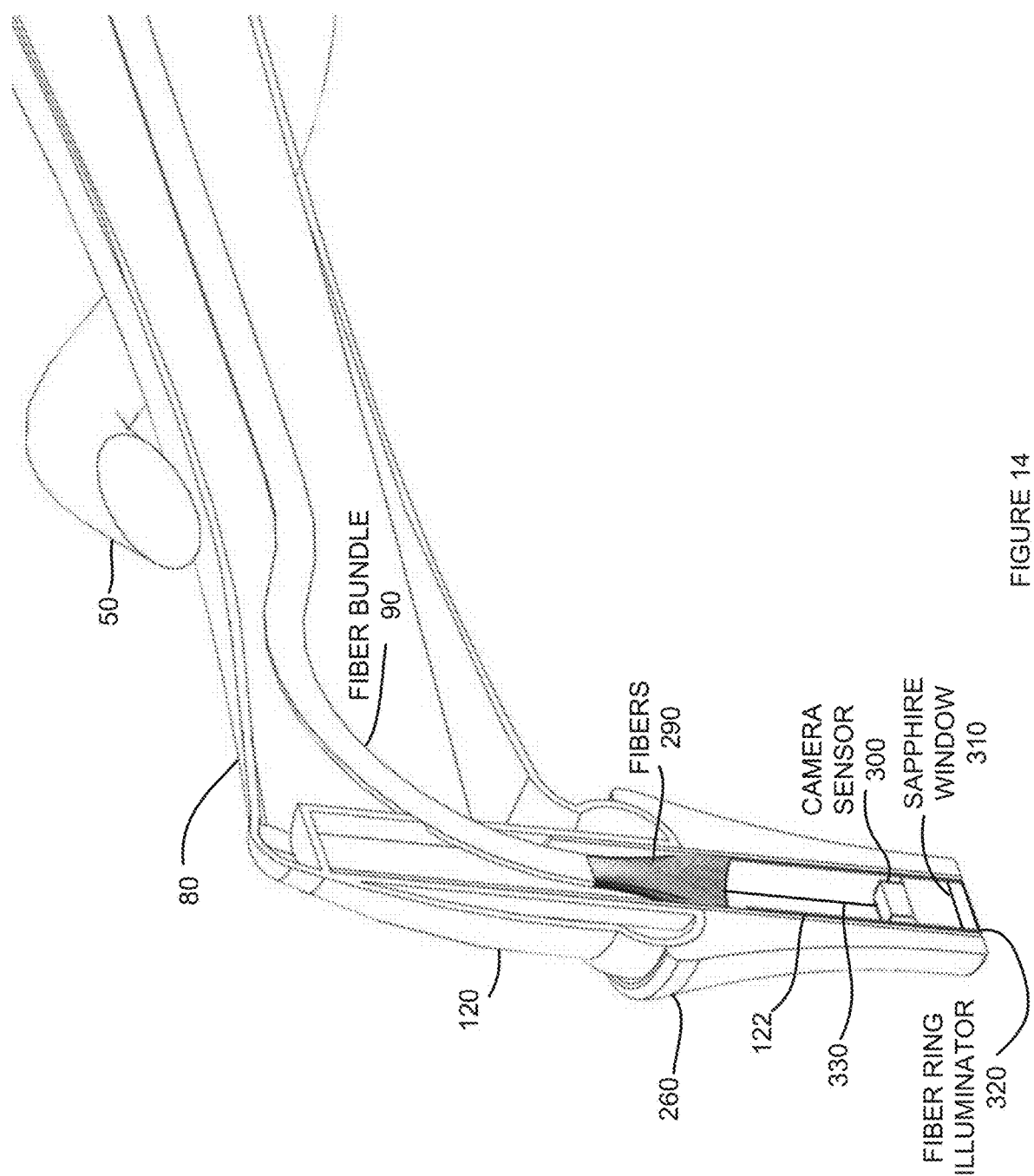
FIG. 14 is a diagrammatic cutaway view, in perspective, of the periodontal endoscope embodiment illustrating at least the fiber ring illuminator, the sapphire window, the camera sensor and the illumination fiber bundle.

FIG. 14 is a diagrammatic fragmentary and partially cutaway view, in elevation, illustrating the embodiment of distal end 80 of imaging handle 20, of FIG. 12, with introducer 260 removably installed thereon, shown here to illustrate details with respect to camera housing 120 and components supported therein. It is noted that introducer blade 266 and tubing 50 are not visible in this cutaway view for illustrative clarity, however, removable introducer 260 is shown as installed.

Figure 15:
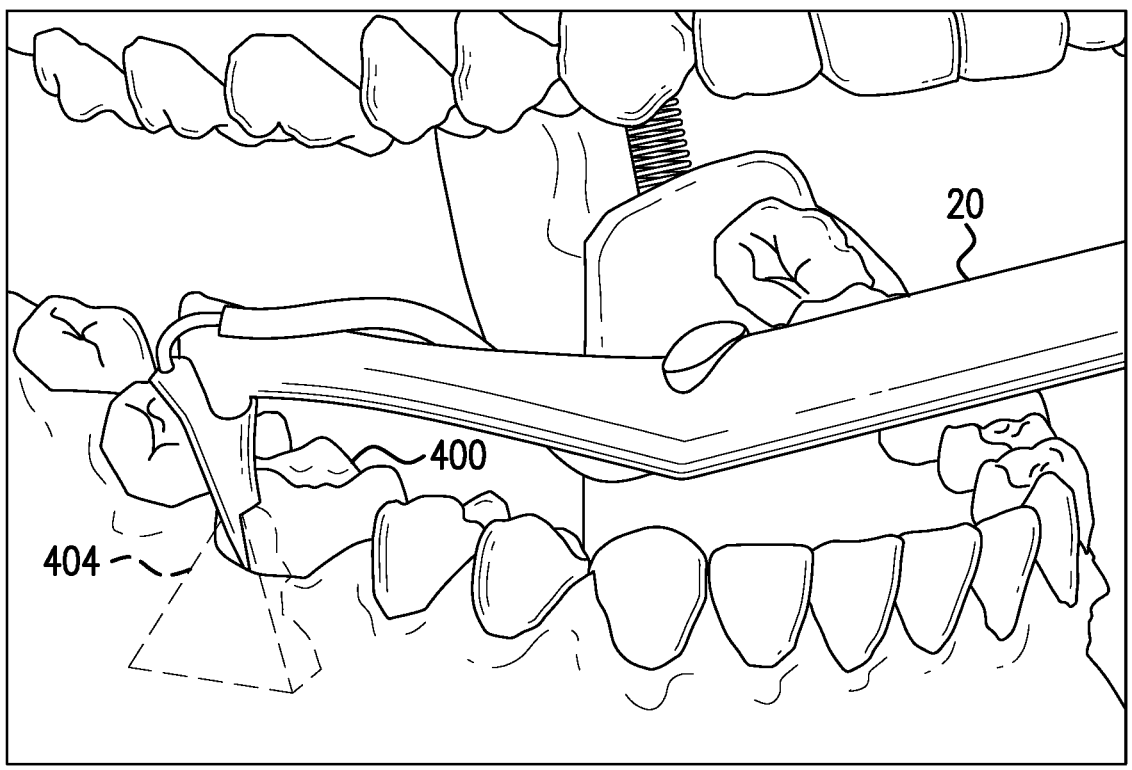
FIG. 15 is a diagrammatic image, in perspective, illustrating the use of an embodiment of the periodontal endoscope of the present disclosure in a dental procedure.
Figure 16:
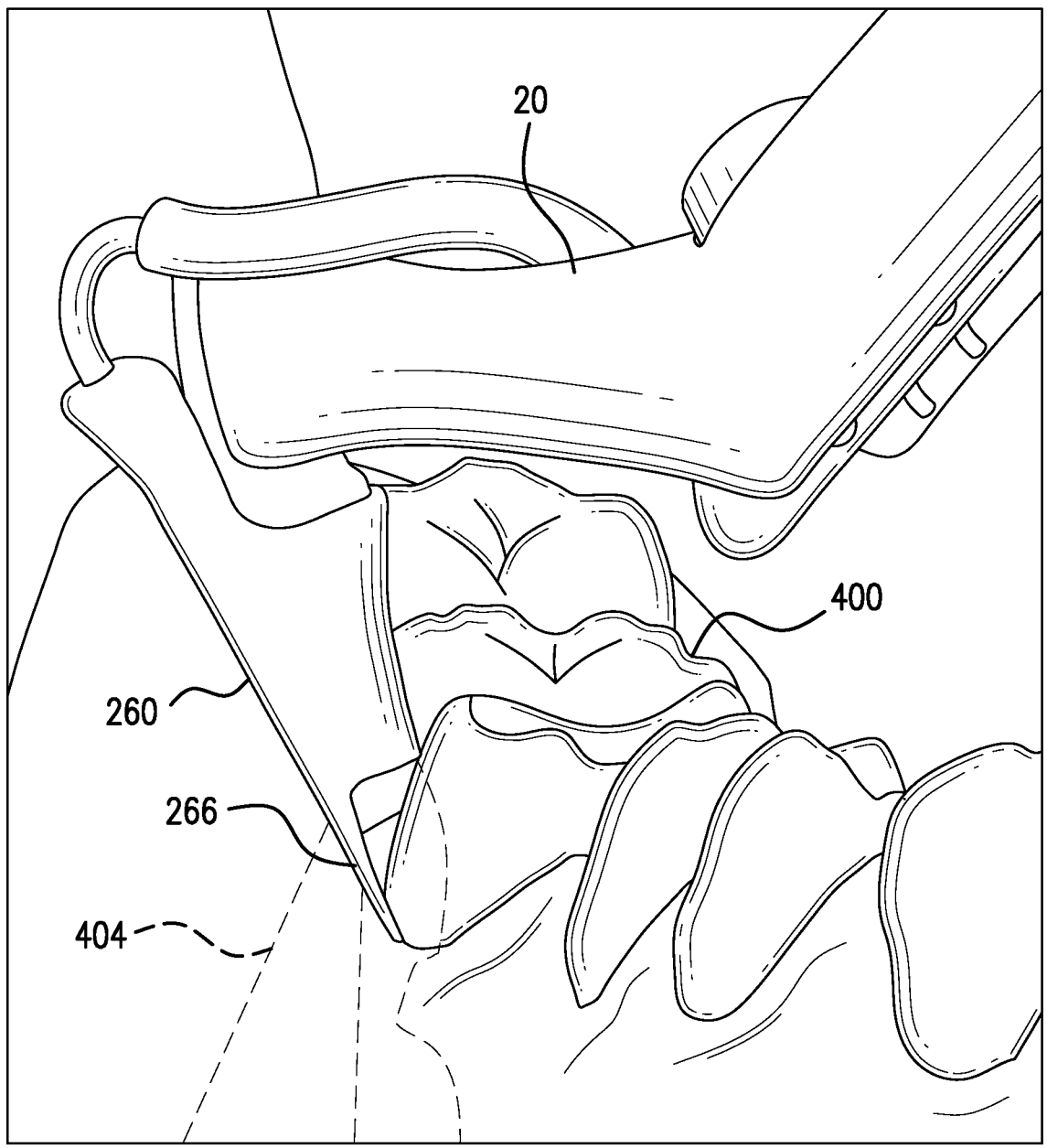
FIG. 16 is another diagrammatic image, in perspective, illustrating the use of the embodiment of the periodontal endoscope of the present disclosure in another dental procedure.

FIGS. 15 and 16 are diagrammatic views, in perspective, of an embodiment, in accordance with the present disclosure, of imaging handle 20 engaging a tooth 400 and gingival tissue 404 of a patient during examination procedures. It is noted that the therapist can readily engage an opposite side of tooth 400 by rotating introducer 260 by 180 degrees.

Figure 17:
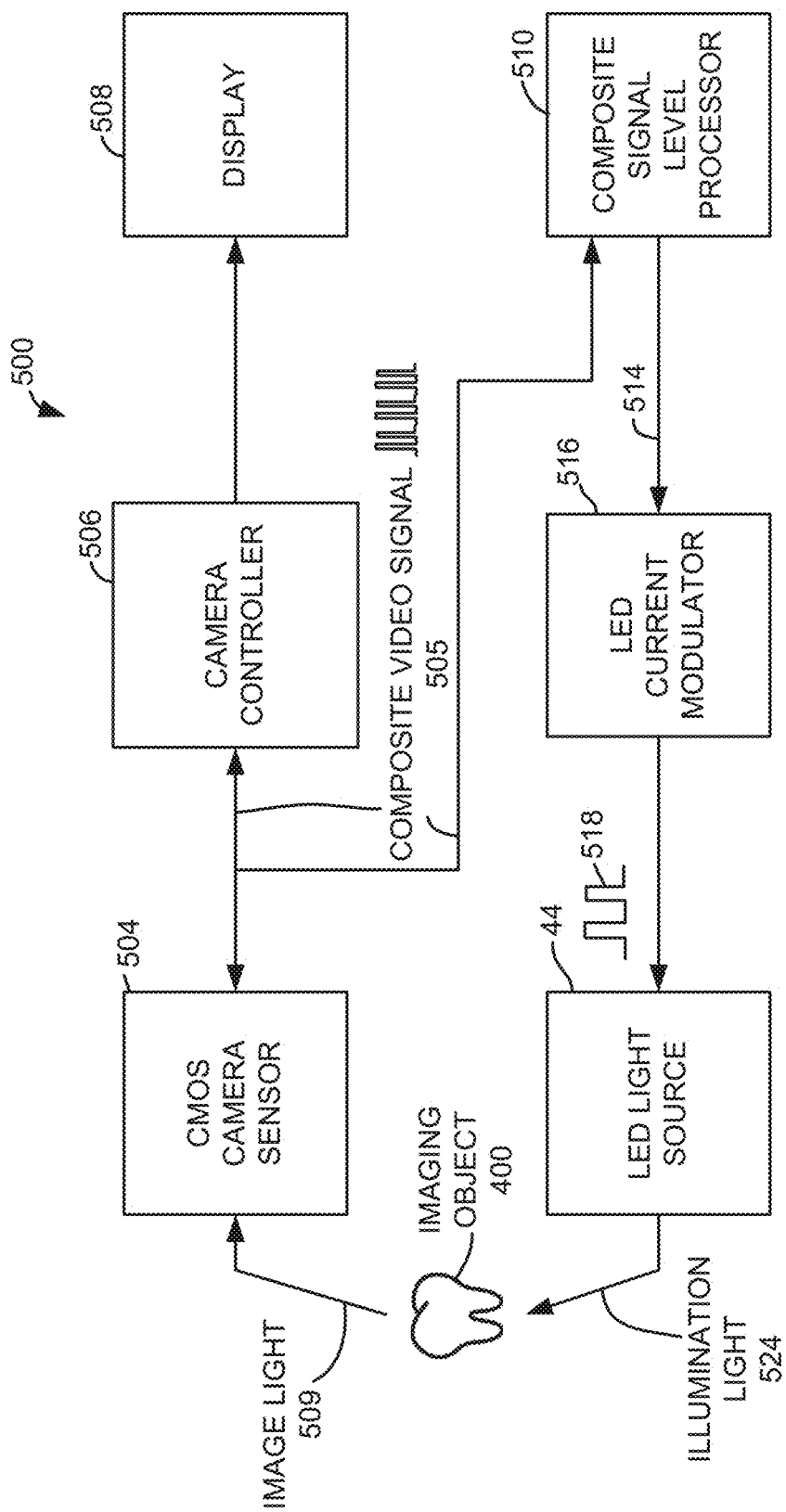
FIG. 17 is a block diagram illustrating an embodiment of a dynamic automatic luminance control system, in accordance with the present disclosure.

Attention is now directed to FIG. 17 which is a block diagram that brings to light an embodiment of a high speed automatic camera illuminance control system, generally indicated by the reference number 500, in accordance with the present disclosure. System 500 includes a suitable imaging sensor 504 having a limited dynamic range such as, for example, a CMOS sensor and an associated camera controller 506 which is in bidirectional communication with camera sensor 504 for producing video signals 505 that are used to drive a display 508 responsive to image light 509. Those of ordinary skill in the art will recognize that the combination of camera sensor 504 and camera controller 506 is, by itself, generally subject to dynamic range limitations. In an embodiment, controller 506 provides a clock signal to sensor 504 to cause the sensor to generate data such as, for example, serial composite data that is returned to the controller. The composite signal can include, for example, a digital framework that at least identifies the start of each frame and an analog signal, between frame or other identifiers (lines, etc.), that is directly proportional to the intensity of incident light on the sensor. On this basis, saturated pixels and under exposed pixels or regions can be identified that are outside the dynamic range of the sensor as well as pixels or and/or regions that have an intensity within the dynamic range or well within the dynamic range of the sensor. Controller 506 can provide some forms of image compensation such as, for example, white balance, barrel distortion and color correction, even in sectors of a frame, however, controller is incapable of addressing and compensating for the range of illumination intensity that is experienced in the apparatus of the periodontal endoscope disclosed herein. With regard to the dynamic range limitations, for a given level of illumination light, highly reflective areas or regions of the field of view can appear as a washed-out bright white (saturated or over exposed) while sufficiently absorbing areas of the field of view can appear as pure black (under exposed). In this regard, prior art CMOS cameras typically utilize automatic exposure control and automatic video gain control to attempt to enable optimal image dynamic range. Unsatisfactory results are typically produced in prior art imaging systems as a result of image adjustment determinations being made based on averaging over the entire image field or averaging over multiple frames. Applicant recognizes that certain imaging systems, including the advanced periodontal endoscope disclosed herein, requires optimal dynamic range to avoid saturation and under exposure of highly reflective areas and low light areas, respectively. In this regard, the image or viewing region is typically in such close proximity to the camera sensor, for example, as close as within a range of 2 millimeters to 15 millimeters, inclusively, that variation in the intensity to which the sensor is exposed, based on reflected light, can be far more extreme than what is seen in other environments at least for the reason that there is little scattering of the reflected light. Even in other typical forms of endoscopy, the intensity variation can be far less with the imaging object one or more inches away or even as close as 15 millimeters. This is not the case, however, when the object being imaged is on the order of only millimeters away from the sensor. Stated in another way, the reflected light can easily be blinding to the sensor and far outside of its available dynamic range. Applicants are unaware of any solution for this concern in the prior art. Applicant further recognizes that fast response time is necessary as the camera scans or advances through a complex medium with wide variation in reflected light. The final result of applying the system brought to light herein is enhanced image clarity over the entire image frame and seamless illumination compensation. In this regard, embodiments of system 500 provide advanced automatic illumination that is submitted to sweep aside the limitations of the prior art, as will be described immediately hereinafter.

Continuing now with the description of FIG. 17, advanced high speed automatic luminance control system 500 further includes illumination light source 44 for illuminating a field of view which, in this non-limiting example, includes tooth 400. During operation, video signal 505 is provided to a composite signal level processor 510 which generates an output 514 that serves as an input for modulator 516 and which at least identifies under exposed and over exposed areas of a portion or unit of the image or frame in real time based on intensity levels that are present in composite video signal 505, as discussed above. Modulator 516 produces a modulated drive signal 518 that specifies or modifies the intensity of illumination light 524 based on the last area or unit of the frame that was illuminated and sampled, if that area exhibits over or under exposure. In this way, composite signal level processor 510 and modulator 516 cooperate to produce an effective dynamic range that is greater than or far greater than the dynamic range of sensor 504 such that essentially no portion of the image that is ultimately generated would be unviewable as a result of the dynamic range limitations of sensor 504. The unit of the frame can be as small as one pixel, although this is not a requirement, but in any event is smaller than one frame of video in order to customize the illumination within each individual frame. Illumination light 524 can be emitted, for example, by optical fiber bundle 90. The modulation signal can be generated in any suitable format, for example, using amplitude, pulse width and/or frequency modulation of current and/or voltage so long as the modulation signal is compatible with the particular illumination light source that is in use. In an embodiment, video signal processor 510 along with light source 44 and modulator 520 exhibit a response time that is sufficiently fast to respond to video signal 505 on a pixel-by-pixel basis in real time as the units of an image frame are sequentially scanned by the system using camera sensor 504. Based on the dynamic luminance level created by stepping through the image frame unit-by-unit, video signal processor 510 drives modulator 520 to modulate the illumination level such that low light units of the image are compensated for by dynamically increasing the illumination intensity while high reflectivity units of the image are compensated for by dynamically reducing the illumination intensity. In this way, the illumination for each unit of the frame is compensated based at least on the last unit of the frame. This process can be applied, for example, on a pixel-by-pixel basis when the unit is a pixel, to a group of pixels as the unit, line-by-line of a video frame when the unit is a line, to a group of lines as the unit and a segment of each frame wherein each frame is made up of a plurality of segments, each of which contains a group of pixels and each segment is of the same shape. A segment, by way of non-limiting example, can be rectangular in shape or even a quadrant of the pixels that make up the overall camera sensor. As discussed above, in an embodiment, illumination can be a function of exposure value (i.e., intensity) determined with respect to a unit of the frame. The exposure value relates to the perceived brightness of RGB (Red Green Blue) color where the perceived brightness can be characterized as 0-100 percent for each RGB component. In some cases, the perceived brightness can be a value represented such as, for example, by 8 bits providing 256 brightness values. The illumination can be modulated to promote image capture that remains within a specified range of values that avoids values that are high as well as avoiding values that are low. For example, a range from 16 to 235 can be targeted or this range can be even further narrowed. In view of this disclosure, it should be clear that the approach of the present Application delivers more complete yet more controlled data across each frame using dynamic illumination, versus prior art processing filters that attempt to improve images after-the-fact with under and over exposed regions resulting from improper illumination. In some embodiments, camera controller 506 and composite signal level processor 510 can be combined into a single chip or package. Such an embodiment can use digital, rather than analog signaling for purposes of transmission of intensity values. Embodiments in accordance with the present Application are submitted to provide sweeping improvements over the existing state-of-the-art with regard to providing improved dynamic range in a very challenging imaging environment.

Figure 18:
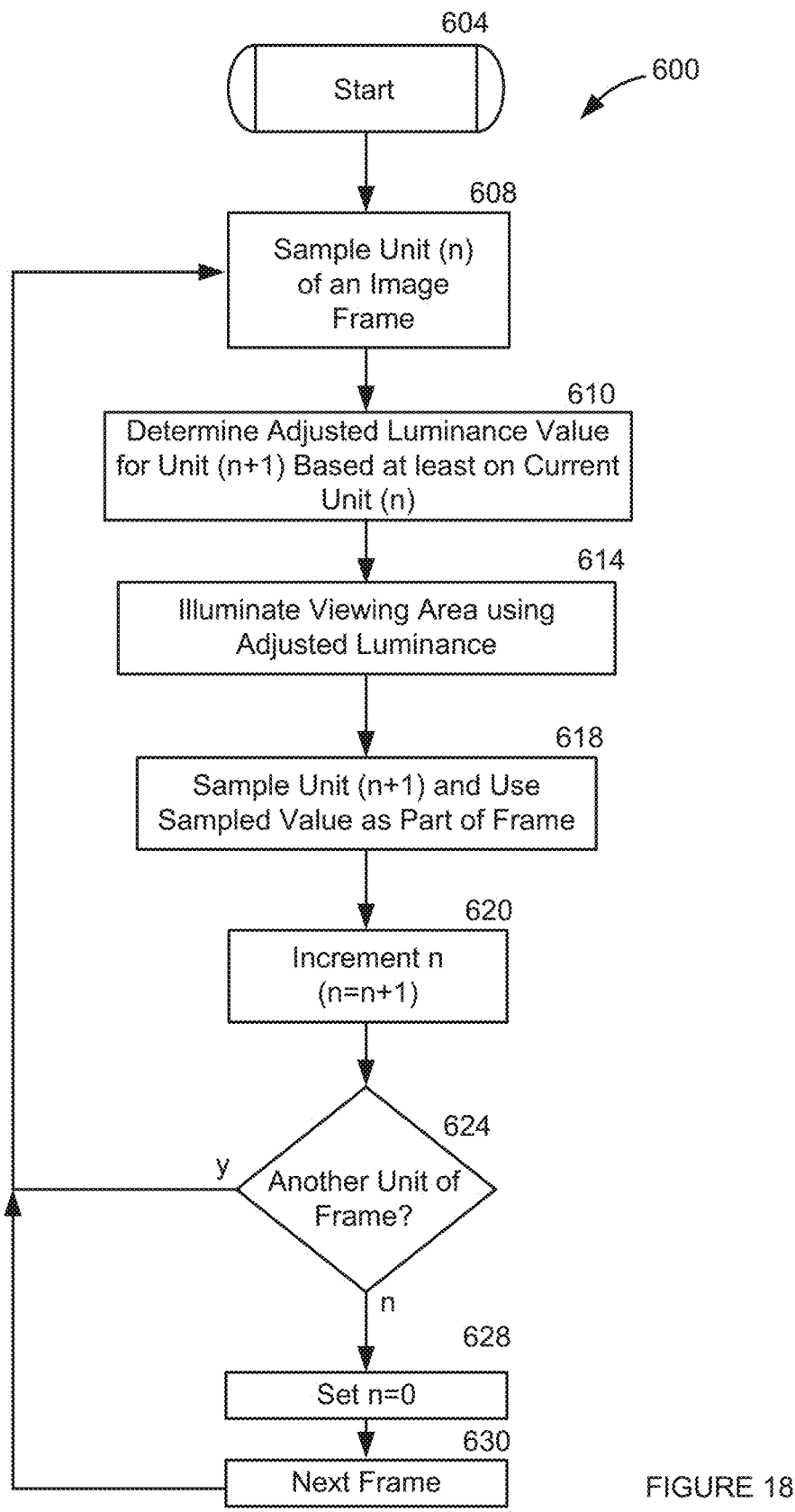
FIG. 18 is a flow diagram illustrating an embodiment of a method for operating the dynamic automatic luminance control system of FIG. 17, in accordance with the present disclosure.

Attention is now directed to FIG. 18 which is a flow diagram, generally indicated by the reference number 600, illustrating an embodiment for the operation of system 10 of the present disclosure. The method starts at 604 and proceeds to 608. At 608, camera sensor 504 is used to sample a unit (n) of a video frame such as, for example, a pixel under a given illumination. For the first pixel, the illumination value can be an estimate such as a middle value of illumination intensity based on the range capability of illumination source 44 and modulator 516. At 610, the luminance level for the next unit (n+1) of the frame is determined at least based on the current unit (n). If current unit (n) was over exposed, the luminance is decreased and if current unit (n) was under exposed, the luminance is increased for the next unit (n+1). In some embodiments, the compensation value for the illumination of the next unit can be based on evaluation of a plurality of prior units such as, for example, an average value or a weighted value. At 614, the viewing area is illuminated based on the adjusted luminance from step 610. At 618, unit (n+1) is sampled or read while illuminated, which sample value can be saved or displayed as part of the frame. At 620, index (n) is incremented. At 624, the availability of another unit for sampling is determined. If the end of the frame has been reached, step 628 sets (n=0), where the value zero points to the first pixel for the next frame. At 630, processing of the next frame initiates by returning to 608. On the other hand, if another unit of the current frame is available, operation returns to 608 which samples the unit identified by index (n). Thus, each frame is sampled and luminance adjusted unit-by-unit which can be pixel-by-pixel or some other incremental amount of a frame.

Figure 19:
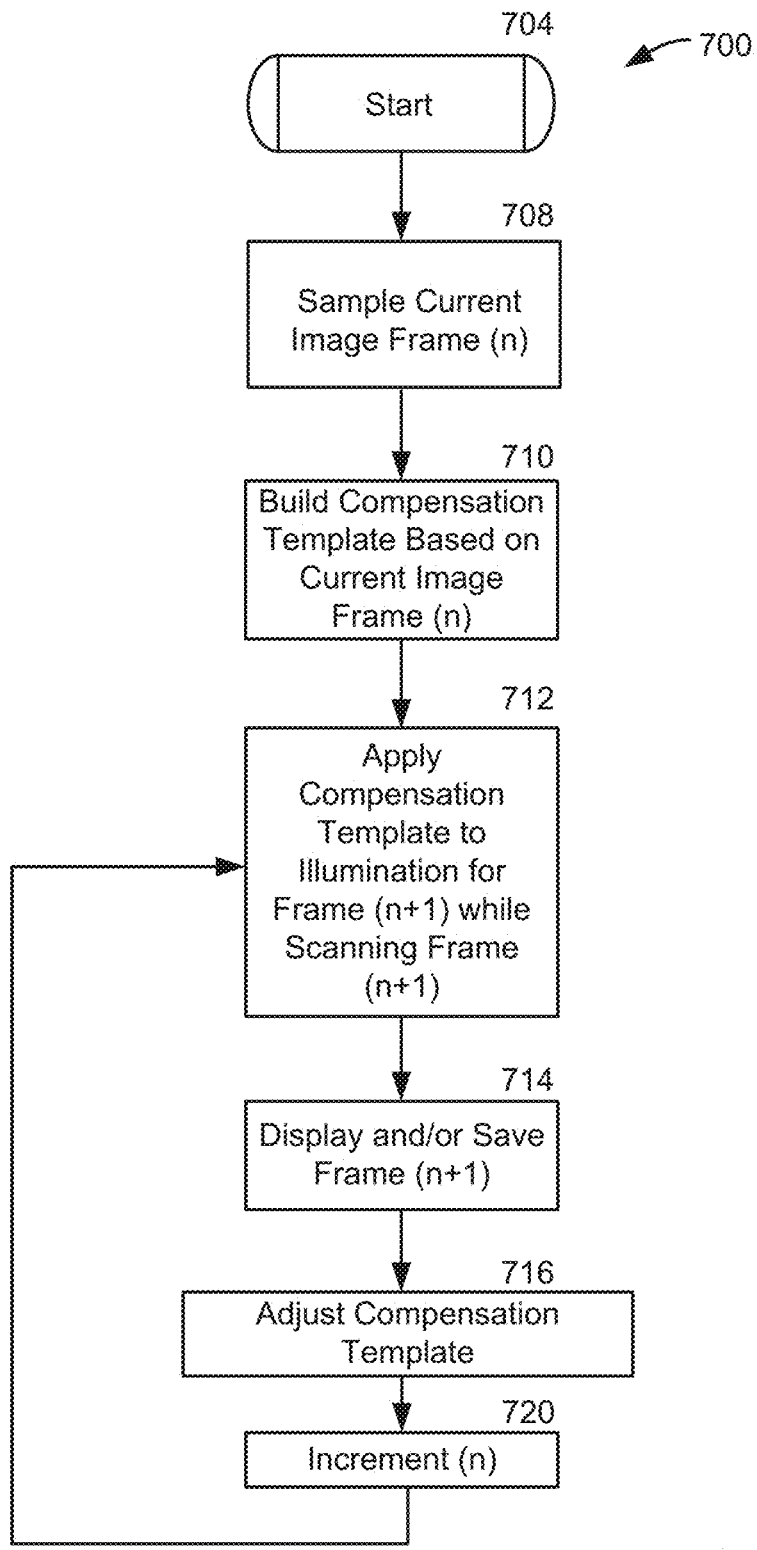
FIG. 19 is a flow diagram illustrating another embodiment of a method for operating the dynamic automatic luminance control system of FIG. 17, in accordance with the present disclosure.

Turning to FIG. 19 another flow diagram is shown, generally indicated by the reference number 700, illustrating another embodiment for the operation of system 10 of the present disclosure. The method starts at 704 and proceeds to 708. At 708, camera sensor 504 is used to sample each unit of a video frame such as, for example, pixel-by-pixel based on an illumination template that defines an illumination value for each unit of the frame which can be an illumination template derived from sampling the last frame that was processed. In the instance of the first frame of a video stream being processed, a mid-point illumination value can be used for all units of the frame based on the illumination intensity range of the illumination source that is in use. At 710, a compensation template is built, which can be an adjusted version of the last template that was used, based on the current sample values of the image frame. At 712, the compensation template is applied to the next frame (n+1) as the frame is scanned unit-by-unit. At 714, the scanned unit values for frame (n+1) can be saved and/or displayed. At 716, the compensation template is adjusted based on the scan values resulting from frame (n+1). At 720, index (n) is incremented and the procedure returns to 712 to apply the adjusted or new compensation template from step 716 to the next frame. Thus, the illumination compensation template can be regenerated frame-by-frame such that the template for a current frame can be applied to customize the illumination of each pixel (or other unit) for the next frame.

Figure 20:
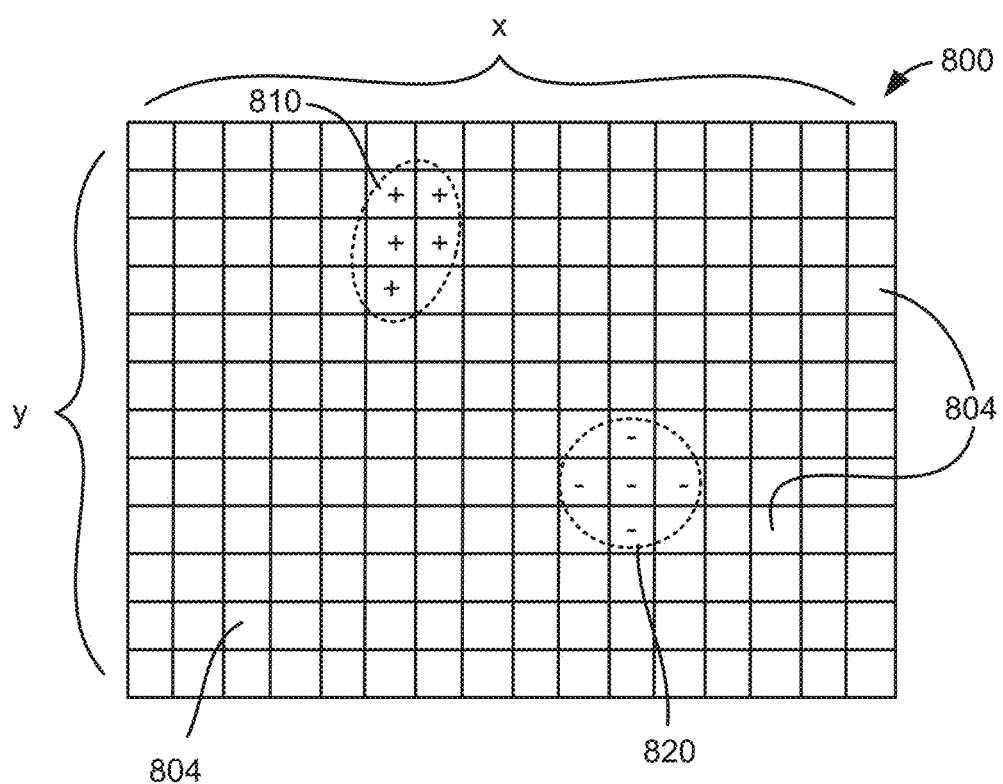
FIG. 20 is a diagrammatic illustration of an illumination template produced in accordance with the method of FIG. 19.

FIG. 20 is a diagrammatic graphical illustration of an illumination compensation template, generally indicated by the reference number 800. For descriptive clarity a number of pixels 804 of the template, some of which have been individually designated, are shown in an x by y array. The illumination compensation template can be a map of the pixel arrangement such as, for example, a two dimensional data structure for a given camera sensor to store an illumination value in association with each pixel. In this example, each one of a first group of pixels 810 includes a plus (+) sign in each pixel indicating that some value of additional luminance will be emitted for each of these pixels during a frame scan while each one of a second group of pixels 820 includes a plus (−) sign in each pixel indicating that a reduced value of luminance will be emitted for each of these pixels during a frame scan. The remaining pixels that are devoid of (+) and (−) designations may have produced acceptable imaging results, for example, using an average value of illuminance or with the same illuminance value from the illuminance template of the last frame. In an embodiment, a plus (+) indication identifies some added illuminance amount (i.e., a positive delta) above some average value up to a maximum capability of the illumination arrangement is needed while a minus (−) indication (i.e., a negative delta) identifies some reduced illuminance amount below some average value is needed. In another embodiment, an illumination value or setting can be specified for each pixel that is within the overall range of illumination capabilities of the illumination arrangement. Of course, the illumination pattern is customized for each frame and can be complex, as compared to the example of FIG. 19.

The foregoing description of the invention has been presented for purposes of illustration and description. It is not intended to be exhaustive or to limit the invention to the precise form or forms disclosed, and other modifications and variations may be possible in light of the above teachings. Accordingly, those of skill in the art will recognize certain modifications, permutations, additions and sub-combinations of the embodiments described above.

What is claimed is:

1. A periodontal endoscope, comprising:
   an imaging handle including a grip portion intermediate between a connection end and an imaging end, the imaging end including a tubular housing that supports a camera sensor therein for imaging a field of view, said connection end at least configured for external electrical connection for providing external electrical power to the camera sensor and for transferring electrical signals including electrical image signals based on imaging of the field of view by the camera sensor to the connection end for external transfer;

an introducer including an introducer blade including a tip and defining a camera channel that receives the camera sensor such that the introducer blade is selectively rotatable around the camera sensor along an arcuate path for engaging gingival tissue in said field of view for any rotational orientation of the introducer blade relative to the camera sensor while the tip of the introducer blade remains in the field of view; and an illumination arrangement including an optical fiber bundle that extends from the connection end to the imaging end for carrying illumination light that is introduced into the optical fiber bundle at the connection end and emitted from the optical fiber bundle at the imaging end to illuminate the field of view.

2. The periodontal endoscope of claim 1 wherein a camera barrel supports the camera sensor and the introducer is rotatably received on the camera barrel for rotation over a full circle of rotation relative to the camera sensor.

3. The periodontal endoscope of claim 1 wherein said introducer blade is configured at least to move marginal gingival tissue away from a tooth and defines an irrigation channel for carrying an irrigation fluid to irrigate the field of view and gingival tissue therein, said introducer configured for coupling with an irrigation tube, having a proximal end that receives the irrigation fluid and a length that carries the irrigation fluid to a distal end that is attached to the introducer in fluid communication with the irrigation channel.

4. The periodontal endoscope of claim 3 wherein said imaging handle defines a passage for removably receiving at least a portion of the length of the irrigation tube.

5. The periodontal endoscope of claim 3 wherein said imaging handle supports an irrigation switch in electrical communication with the connection end for operator actuation of the irrigation switch to cause a flow of the irrigation fluid.

6. The periodontal endoscope of claim 1 wherein the optical fiber bundle includes a plurality of optical fibers and the plurality of optical fibers are arranged at the imaging end to surround the tubular housing such that the illumination light is emitted from an annular area proximate the imaging end.

7. The periodontal endoscope of claim 6 wherein the tubular housing supports a lens for focusing light from the field of view onto a camera sensor of the camera.

8. The periodontal endoscope of claim 7 wherein the plurality of optical fibers surround said lens outward of the tubular housing.

9. The periodontal endoscope of claim 6 wherein a distal end of the tubular housing is sealed by a window.

10. The periodontal endoscope of claim 9 wherein the window is a sapphire window.

11. The periodontal endoscope of claim 10 wherein the plurality of optical fibers surround said sapphire widow outward of the tubular housing to define said annular area.

12. A periodontal endoscopic imaging system, comprising:

the periodontal endoscope of claim 1;
a console further comprising:
a display for displaying the field of view based on the electrical image signals; and
an illumination light source to produce illumination light that is coupled to an umbilical to carry the illumination light to an umbilical connector that is complementary to the connection end of the imaging handle to couple the illumination light into the optical fiber bundle when the umbilical connector is removably attached to the connection end.

13. The periodontal imaging system of claim 12 wherein the connection end of the imaging handle and the umbilical connector are cooperatively configured for removable magnetic coupling.

14. The periodontal imaging system of claim 13 wherein the umbilical connector supports a ring magnet to provide said removable magnetic coupling.

15. The periodontal imaging system of claim 12 wherein the umbilical includes an umbilical fiber optic bundle that carries the illumination light from the illumination light source to the umbilical connector for optical coupling to the optical fiber bundle.

16. The periodontal imaging system of claim 15 wherein the umbilical optic fiber bundle is optically butt coupled to the optical fiber bundle when the connection end of the imaging handle magnetically couples to the umbilical end of the umbilical.

17. The periodontal imaging system of claim 12 wherein the umbilical carries a plurality of electrical conductors extending from the console to a set of electrical contacts supported at the umbilical connector for electrical connection to a complementary set of electrical contacts supported by the connection end of the imaging handle for coupling the external electrical power for said camera and for coupling the electrical image signals based on imaging of the field of view by the camera sensor to the console for presentation on said display.

18. The periodontal imaging system of claim 17 wherein the umbilical connector and the connection end of the imaging handle include a registration arrangement for indexing the set of electrical contacts of the umbilical connector to the complementary set of electrical contacts supported by the connection end of the imaging handle.

19. The periodontal imaging system of claim 12, further comprising:

a controller located in one of said console and said imaging handle for driving the camera sensor to produce the electrical image signals that are transferred to the connection end of the imaging handle.

* * * * *